United States Patent
Takeshima et al.

(10) Patent No.: US 7,479,383 B2
(45) Date of Patent: *Jan. 20, 2009

(54) MODIFIED PYRROLOQUINOLINE QUINONE (PQQ) DEPENDENT GLUCOSE DEHYDROGENASE EXCELLENT IN SUBSTRATE SPECIFICITY

(75) Inventors: Seiji Takeshima, Tsuruga (JP);
Tadanobu Matsumura, Tsuruga (JP);
Takahide Kishimoto, Tsuruga (JP);
Masanori Oka, Tsuruga (JP); Noriaki Hirayama, Zama (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 58 days.

This patent is subject to a terminal disclaimer.

(21) Appl. No.: 10/570,904

(22) PCT Filed: Aug. 31, 2004

(86) PCT No.: PCT/JP2004/012508

§ 371 (c)(1),
(2), (4) Date: Jun. 6, 2006

(87) PCT Pub. No.: WO2005/026340

PCT Pub. Date: Mar. 24, 2005

(65) Prior Publication Data

US 2007/0105173 A1    May 10, 2007

(30) Foreign Application Priority Data

| Sep. 8, 2003 | (JP) | ............................. | 2003-315797 |
| Sep. 8, 2003 | (JP) | ............................. | 2003-315799 |
| Mar. 4, 2004 | (JP) | ............................. | 2004-060282 |
| Mar. 4, 2004 | (JP) | ............................. | 2004-060283 |
| May 21, 2004 | (JP) | ............................. | 2004-151905 |

(51) Int. Cl.
C12N 9/04 (2006.01)
C12N 1/20 (2006.01)
C12N 15/00 (2006.01)
C12Q 1/00 (2006.01)
C12Q 21/04 (2006.01)
C12Q 1/32 (2006.01)
C07H 21/04 (2006.01)
C12Q 1/68 (2006.01)

(52) U.S. Cl. ............................. 435/190; 435/4; 435/6; 435/26; 435/69.1; 435/71.1; 435/440; 435/252.3; 435/320.1; 536/23.2

(58) Field of Classification Search .................. None
See application file for complete search history.

(56) References Cited

U.S. PATENT DOCUMENTS 6,103,509 A * 8/2000 Sode .......................... 435/190
2003/0232418 A1  12/2003  Takeshima et al.

FOREIGN PATENT DOCUMENTS

| EP | 1 167 519 A1 | 1/2002 |
| EP | 1 176 202 A1 | 1/2002 |
| EP | 1 367 120 A2 | 12/2003 |
| EP | 1 369 485 A1 | 12/2003 |
| JP | 10-243786 A | 9/1998 |
| JP | 11-243949 A | 9/1999 |
| JP | 2000-262281 A | 9/2000 |
| JP | 2000-312588 A | 11/2000 |
| JP | 2000-350588 A | 12/2000 |
| JP | 2001-037483 A | 2/2001 |
| JP | 2001-197888 A | 7/2001 |
| JP | 2001-346587 A | 12/2001 |
| JP | 2004-173538 A | 6/2004 |
| WO | WO 02/34919 A1 | 5/2002 |
| WO | WO 02/072839 A1 | 9/2002 |
| WO | WO 03/027294 A1 | 4/2003 |
| WO | WO 03/106668 A1 | 12/2003 |
| WO | WO 2004/005499 A1 | 1/2004 |

OTHER PUBLICATIONS

Branden et al. Introduction to Protein Structure, Garland Publishing Inc., New York, p. 247, 1991.*
Bak et al., *Biochimica et Biophysica Acta*, 139: 265-276 (1967).
Bak et al., *Biochimica et Biophysica Acta*, 139: 277-293 (1967).
Bak et al., *Biochimica et Biophysica Acta*, 139: 317-327 (1967).
Bak et al., *Biochimica et Biophysica Acta*, 139: 328-335 (1967).

(Continued)

*Primary Examiner*—Yong D Pak
(74) *Attorney, Agent, or Firm*—Leydig, Voit & Mayer, Ltd.

(57) ABSTRACT

PQQGDH having an improved substrate specificity or having an improved specific activity in an assay system using ferricyanide ion as a mediator is provided. Modified PQQGDH having the enhanced substrate specificity by introducing an amino acid mutation in a particular region of PQQGDH, and a method of enhancing the specific activity compared with a wild type in the assay system using the ferricyanide ion as the mediator by deleting, substituting, or adding one or more amino acids in an amino acid sequence of the wild type pyrroloquinoline quinone dependent glucose dehydrogenase.

9 Claims, 5 Drawing Sheets

OTHER PUBLICATIONS

Cleton-Jansen et al., *Journal of Bacteriology*, 170(5): 2121-2125 (May 1988).
Muller et al., *Archives of Microbiology*, 144: 151-157 (1986).
Database EMBL 'Online!, retrieved from EBI, Database accession No. AAZ25630, XP002254119, Toyobo Co Ltd (abstract of JP 11 243949 A) (Dec. 23, 1999).
Database EMBL 'Online!, retrieved from EBI, Database accession No. E28182, XP002254120, Toyobo Co Ltd (abstract of JP 11 243949 A) (Feb. 22, 2001).
Database EMBL 'Online!, retrieved from EBI, Database accession No. E73901, XP002254121, Toyobo Co Ltd (abstract of JP 11 243949 A) (Feb. 22, 2001).
Database EMBL 'Online!, retrieved from EBI, Database accession No. AAY45178, XP002254122, Toyobo Co Ltd (abstract of JP 11 243949 A) (Feb. 22, 2001).
Igarashi et al., *Biochemical and Biophysical Research Communications*, 264: 820-824 (1999).
Oubrie et al., *J. Mol. Biol.*, 289: 319-333 (1999).
Oubrie et al., *PNAS*, 96 (21): 11787-11791 (1999).
Oubrie et al., *The EMBO Journal*, 18 (19): 5187-5194 (1999).
Oubrie et al., *Protein Science*, 9: 1265-1273 (2000).
Sode et al., *Enzyme and Microbial Technology*, 26: 491-496 (2000).
Sode et al., *FEBS Letters*, 364(3): 325-327 (1995).
Sode et al., *Biotechnology Letters*, 18(9): 997-1002 (1996).
Sode et al., *Biotechnology Letters*, 19(11): 1073-1077 (1997).
Sode et al., *Biotechnology Letters*, 21(8): 707-710 (1999).
Sode et al., *Biocatalysts and Biotransformation*, 20(6): 405-412 (2002).
Takahashi et al. *Electrochemistry*(Tokyo), 68(11): 907-911 (2000).
Witarto et al., *Applied Biochemistry and Biotechnology*, 77-79: 159-168 (1999).
Yamazaki et al., *Analytical Chemistry*, 72(19): 4689-4693 (2000).
Yoshida et al., *Protein Engineering*, 12(1): 63-70 (1999).
Yoshida et al., *Biotechnology Letters*, 22(18): 1505-1510 (2000).

\* cited by examiner

SEQUENCE LISTING

<160> NUMBER OF SEQ ID NOS: 94

<210> SEQ ID NO 1
<211> LENGTH: 455
<212> TYPE: PRT
<213> ORGANISM: Acinetobacter baumannii

<400> SEQUENCE: 1

Asp Ile Pro Leu Thr Pro Ala Gln Phe Ala Lys Ala Lys Thr Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Val Ser Gly Ser Ala Lys Thr Val Phe
    50                  55                  60

Gln Val Pro Glu Ile Val Ser Asp Ala Asp Gly Gln Asn Gly Leu Leu
65                  70                  75                  80

Gly Phe Ala Phe His Pro Asp Phe Lys His Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Thr Thr Asp Thr Phe
        115                 120                 125

Glu Lys Pro Ile Asp Leu Ile Ala Gly Leu Pro Ser Ser Lys Asp His

```
                130                 135                 140
Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Ser Lys Asp Tyr
                180                 185                 190

His Thr Tyr Met Gly Lys Val Leu Arg Leu Asn Leu Asp Gly Ser Val
                195                 200                 205

Pro Lys Asp Asn Pro Ser Phe Asn Gly Val Val Ser His Ile Tyr Thr
210                 215                 220

Leu Gly His Arg Asn Pro Gln Gly Leu Ala Phe Ala Pro Asn Gly Lys
225                 230                 235                 240

Leu Leu Gln Ser Glu Gln Gly Pro Asn Ser Asp Asp Glu Ile Asn Leu
                245                 250                 255

Val Leu Lys Gly Gly Asn Tyr Gly Trp Pro Asn Val Ala Gly Tyr Lys
                260                 265                 270

Asp Asp Ser Gly Tyr Ala Tyr Ala Asn Tyr Ser Ala Ala Thr Asn Lys
                275                 280                 285

Ser Gln Ile Lys Asp Leu Ala Gln Asn Gly Ile Lys Val Ala Thr Gly
                290                 295                 300

Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
                325                 330                 335

Pro Thr Cys Gly Glu Met Ala Tyr Ile Cys Trp Pro Thr Val Ala Pro
                340                 345                 350

Ser Ser Ala Tyr Val Tyr Thr Gly Gly Lys Lys Ala Ile Pro Gly Trp
                355                 360                 365

Glu Asn Thr Leu Leu Val Pro Ser Leu Lys Arg Gly Val Ile Phe Arg
                370                 375                 380

Ile Lys Leu Asp Pro Thr Tyr Ser Thr Thr Leu Asp Asp Ala Ile Pro
385                 390                 395                 400

Met Phe Lys Ser Asn Asn Arg Tyr Arg Asp Val Ile Ala Ser Pro Glu
                405                 410                 415

Gly Asn Thr Leu Tyr Val Leu Thr Asp Thr Ala Gly Asn Val Gln Lys
                420                 425                 430

Asp Asp Gly Ser Val Thr His Thr Leu Glu Asn Pro Gly Ser Leu Ile
                435                 440                 445

Lys Phe Thr Tyr Asn Gly Lys
    450                 455

<210> SEQ ID NO 2
<211> LENGTH: 1368
<212> TYPE: DNA
<213> ORGANISM: Acinetobacter baumannii

<400> SEQUENCE: 2 gatataccctc tgacacctgc tcagttcgca aaagcgaaaa cagaaaattt tgataaaaaa     60
gtgattctgt ccaatttaaa taaaccacat gctttgttat ggggggccaga taatcaaatt    120 tggttaaccg aacgtgcaac tggcaaaatt ttaagagtaa atcctgtatc tggtagcgcg    180
aaaacagtat ttcaggttcc tgaaattgtg agtgatgctg atgggcaaaa tggttttgtta   240 ggttttgctt ttcatcctga ctttaaacat aaccccttata tctatatttc aggcacttttt   300
```

-continued

```
aaaaatccaa aatctacaga taaagagtta cctaatcaga cgattattcg tagatatacc    360
tataataaaa ctacagatac atttgaaaag cctattgatt tgattgcagg tttaccgtca    420
tcaaaagatc atcagtctgg tcgtctcgtt attggtccag accaaaaaat ctactatacg    480
attggtgacc aaggtcgtaa tcagttagct tatctgttct taccgaatca ggcacagcat    540
actccgactc agcaagagct caatagtaaa gactaccata catatatggg taaagtatta    600
cgcttaaatc tggacggcag tgtacctaaa gacaacccaa gctttaacgg cgtagtgagt    660
catatctaca ctttagggca ccgtaatcca caaggtttag catttgcccc aaatggaaag    720
cttttacaat ctgagcaagg accaaattct gatgatgaaa ttaaccttgt attaaaaggt    780
ggtaactatg ctggccaaa tgtagctggt tataaagatg acagtggtta tgcctatgca    840
aactattcgg cagcaaccaa taatcacaa attaaagatt tagctcaaaa cgggataaaa    900
gtagcaacag tgttcctgt gactaaagag tctgaatgga ctggtaaaaa ctttgtgccg    960
cctttgaaaa ctttatatac ggtacaagat acctataact ataatgaccc tacttgtggt   1020
gagatggcat atatttgctg ccaacggtt gcaccgtcat cagcatatgt atatacggga   1080
ggcaaaaaag cgattccagg gtgggaaaat acattattgg tcccatcttt aaaacgtggg   1140
gtgattttcc gtattaaatt ggacccgaca tatagcacga ctttggatga tgctatccca   1200
atgtttaaaa gcaataaccg ttatcgtgat gtcatcgcta gtccagaagg taataccta    1260 tatgtgctga ctgatacagc ggggaatgta caaaaagatg atggttctgt cactcatact   1320
ttagagaatc ccggttctct cattaaattt acatataacg gtaagtaa                1368
```

```
<210> SEQ ID NO 3
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 3
agtgatgctg atgggaataa tggtttgtta ggt                                  33

<210> SEQ ID NO 4
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 4
agtgatgctg atggggagaa tggtttgtta ggt                                  33

<210> SEQ ID NO 5
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 5
agtgatgctg atgggacaaa tggtttgtta ggt                                  33

<210> SEQ ID NO 6
<211> LENGTH: 33
<212> TYPE: DNA
<213> ORGANISM: Artificial Sequence
<220> FEATURE:
```

-continued

```
<223> OTHER INFORMATION: Artificial Sequence oligonucleotide

<400> SEQUENCE: 6
agtgatgctg atgggatgaa tggtttgtta ggt                          33

<210> SEQ ID NO 7
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 7
agtgatgctg atgggggaa tggtttgtta ggt                           33

<210> SEQ ID NO 8
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 8
agtgatgctg atgggaagaa tggtttgtta ggt                          33

<210> SEQ ID NO 9
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 9
gaccaaggtc gtaatatttt agcttatctg ttc                          33

<210> SEQ ID NO 10
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 10
gaccaaggtc gtaatgtatt agcttatctg ttc                          33

<210> SEQ ID NO 11
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 11
gaccaaggtc gtaatgcatt agcttatctg ttc                          33

<210> SEQ ID NO 12
<211> LENGTH: 43
<212> TYPE: DNA
<213> ORGANISM: Artificial Sequence
<220> FEATURE:
<223> OTHER INFORMATION: Artificial Sequence oligonucleotide

<400> SEQUENCE: 12
cgaatcaggc acagcatact ccgactcagc aagagctcaa tag               43
```

<210> SEQ ID NO 13
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(25)
<223> OTHER INFORMATION: "n stands for any base"

<400> SEQUENCE: 13
gtaagaacag ataagcnnnn nnnnnacgac cttggtcacc aatcg         45

<210> SEQ ID NO 14
<211> LENGTH: 40
<212> TYPE: DNA
<213> ORGANISM: Artificial Sequence
<220> FEATURE:
<223> OTHER INFORMATION: Artificial Sequence oligonucleotide

<400> SEQUENCE: 14
gatgctgatg ggcaaaatgg tttgttaggt tttgcttttc              40

<210> SEQ ID NO 15
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(15)
<223> OTHER INFORMATION: "n stands for any base"

<400> SEQUENCE: 15
actcacnnnn nnnnnaacct gaaatactgt tttcgcgc                38

<210> SEQ ID NO 16
<211> LENGTH: 50
<212> TYPE: DNA
<213> ORGANISM: Artificial Sequence
<220> FEATURE:
<223> OTHER INFORMATION: Artificial Sequence oligonucleotide

<400> SEQUENCE: 16
tttaccgtca tcaaaagatc atcagtctgg tcgtctcgtt attggtccag    50

<210> SEQ ID NO 17
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(26)
<223> OTHER INFORMATION: "n stands for any base"

<400> SEQUENCE: 17
cctgcaatca aatcaatnnn nnnnnnaaat gtatctgtag ttttattata gg    52

<210> SEQ ID NO 18
<211> LENGTH: 39
<212> TYPE: DNA
<213> ORGANISM: Artificial Sequence
<220> FEATURE:
<223> OTHER INFORMATION: Artificial Sequence oligonucleotide

```
<400> SEQUENCE: 18 acgttgcac cgtcatcagc atatgtatat acgggaggc                                      39

<210> SEQ ID NO 19
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(24)
<223> OTHER INFORMATION: "n stands for any base"

<400> SEQUENCE: 19
tggccagcaa atatannnnn nnnnaccaca agtagggtc                                     39

<210> SEQ ID NO 20
<211> LENGTH: 34
<212> TYPE: DNA
<213> ORGANISM: Artificial Sequence
<220> FEATURE:
<223> OTHER INFORMATION: Artificial Sequence oligonucleotide

<400> SEQUENCE: 20
atggttctgt cactcatact ttagagaatc ccgg                                          34

<210> SEQ ID NO 21
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(19)
<223> OTHER INFORMATION: "n stands for any base"

<400> SEQUENCE: 21 catcttttg tacattnnnc cccgctgtat cagtc                                          35

<210> SEQ ID NO 22
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 22
ttaccgaatc aggcacagca tactccgact cag                                           33

<210> SEQ ID NO 23
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 23
gaacagataa gctaagcaat tacgaccttg gtc                                           33

<210> SEQ ID NO 24
<211> LENGTH: 33
<212> TYPE: DNA
<213> ORGANISM: Artificial Sequence
<220> FEATURE:
<223> OTHER INFORMATION: Artificial Sequence oligonucleotide
```

<400> SEQUENCE: 24
gaacagataa gctaartcat tacgaccttg gtc          33

<210> SEQ ID NO 25
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 25
gaacagataa gctaaytcat tacgaccttg gtc          33

<210> SEQ ID NO 26
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 26
gaacagataa gctaaraaat tacgaccttg gtc          33

<210> SEQ ID NO 27
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 27
gaacagataa gctaagccat tacgaccttg gtc          33

<210> SEQ ID NO 28
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 28
gaacagataa gctaartgat tacgaccttg gtc          33

<210> SEQ ID NO 29
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 29
gaacagataa gctaayttat tacgaccttg gtc          33

<210> SEQ ID NO 30
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: "n stands for any base"

<400> SEQUENCE: 30
gaacagataa gctaanagat tacgaccttg gtc                                33

<210> SEQ ID NO 31
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 31
gaacagataa gctaacatat tacgaccttg gtc                                33

<210> SEQ ID NO 32
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 32
gaacagataa gctaarttat tacgaccttg gtc                                33

<210> SEQ ID NO 33
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: "n stands for any base"

<400> SEQUENCE: 33
gaacagataa gctaanggat tacgaccttg gtc                                33

<210> SEQ ID NO 34
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: "n stands for any base"

<400> SEQUENCE: 34
gaacagataa gctaancgat tacgaccttg gtc                                33

<210> SEQ ID NO 35
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 35
gaacagataa gctaagctat tacgaccttg gtc                                33

<210> SEQ ID NO 36
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 36

```
gaacagataa gctaacgtat tacgaccttg gtc                                    33

<210> SEQ ID NO 37
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 37
gaacagataa gctaaccaat tacgaccttg gtc                                    33

<210> SEQ ID NO 38
<211> LENGTH: 33
<212> TYPE: DNA
<213> ORGANISM: Artificial Sequence
<220> FEATURE:
<223> OTHER INFORMATION: Artificial Sequence oligonucleotide

<400> SEQUENCE: 38
gaacagataa gctaartaat tacgaccttg gtc                                    33

<210> SEQ ID NO 39
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 39
gaccaaggtc gtaatcaggc agcttatctg ttcttaccg                              39

<210> SEQ ID NO 40
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 40
gaccaaggtc gtaatcaggt tgcttatctg ttcttaccg                              39

<210> SEQ ID NO 41
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 41
gaccaaggtc gtaatcagta tgcttatctg ttcttaccg                              39

<210> SEQ ID NO 42
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 42
gaccaaggtc gtaatcagca tgcttatctg ttcttaccg                              39

<210> SEQ ID NO 43
<211> LENGTH: 39
<212> TYPE: DNA
```

```
<213> ORGANISM: Artificial Sequence
<220> FEATURE:
<223> OTHER INFORMATION: Artificial Sequence oligonucleotide

<400> SEQUENCE: 43
gaccaaggtc gtaatcagaa agcttatctg ttcttaccg                      39

<210> SEQ ID NO 44
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 44
gaccaaggtc gtaatcagga tgcttatctg ttcttaccg                      39

<210> SEQ ID NO 45
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 45
gaccaaggtc gtaatcagtc agcttatctg ttcttaccg                      39

<210> SEQ ID NO 46
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 46
gaccaaggtc gtaatcagaa tgcttatctg ttcttaccg                      39

<210> SEQ ID NO 47
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 47
gaccaaggtc gtaatcaggg agcttatctg ttcttaccg                      39

<210> SEQ ID NO 48
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 48
gaccaaggtc gtaatcagtg tgcttatctg ttcttaccg                      39

<210> SEQ ID NO 49
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: "n stands for any base"
```

<400> SEQUENCE: 49
gtaagaacag ataagcngat gcattacgac cttggtcacc aatcg                45

<210> SEQ ID NO 50
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 50
gtaagaacag ataagcrcat gcattacgac cttggtcacc aatcg                45

<210> SEQ ID NO 51
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 51
gtaagaacag ataagcytct gcattacgac cttggtcacc aatcg                45

<210> SEQ ID NO 52
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 52
gtaagaacag ataagcraat gcattacgac cttggtcacc aatcg                45

<210> SEQ ID NO 53
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 53
gtaagaacag ataagcrtgt gcattacgac cttggtcacc aatcg                45

<210> SEQ ID NO 54
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 54
gtaagaacag ataagcdatt gcattacgac cttggtcacc aatcg                45

<210> SEQ ID NO 55
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 55
gtaagaacag ataagcyttt gcattacgac cttggtcacc aatcg                45

<210> SEQ ID NO 56

<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 56
gtaagaacag ataagccatt gcattacgac cttggtcacc aatcg                45

<210> SEQ ID NO 57
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 57
gtaagaacag ataagcrttt gcattacgac cttggtcacc aatcg                45

<210> SEQ ID NO 58
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: "n stands for any base"

<400> SEQUENCE: 58
gtaagaacag ataagcnggt gcattacgac cttggtcacc aatcg                45

<210> SEQ ID NO 59
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 59
gtaagaacag ataagcytgt gcattacgac cttggtcacc aatcg                45

<210> SEQ ID NO 60
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: "n stands for any base"

<400> SEQUENCE: 60
gtaagaacag ataagcncgt gcattacgac cttggtcacc aatcg                45

<210> SEQ ID NO 61
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: "n stands for any base"

<400> SEQUENCE: 61
gtaagaacag ataagcngat gcattacgac cttggtcacc aatcg    45

<210> SEQ ID NO 62
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: "n stands for any base"

<400> SEQUENCE: 62
gtaagaacag ataagcngtt gcattacgac cttggtcacc aatcg    45

<210> SEQ ID NO 63
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: "n stands for any base"

<400> SEQUENCE: 63
gtaagaacag ataagcnact gcattacgac cttggtcacc aatcg    45

<210> SEQ ID NO 64
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 64
gtaagaacag ataagcccat gcattacgac cttggtcacc aatcg    45

<210> SEQ ID NO 65
<211> LENGTH: 45
<212> TYPE: DNA
<213> ORGANISM: Artificial Sequence
<220> FEATURE:
<223> OTHER INFORMATION: Artificial Sequence oligonucleotide

<400> SEQUENCE: 65
gtaagaacag ataagcrtat gcattacgac cttggtcacc aatcg    45

<210> SEQ ID NO 66
<211> LENGTH: 36
<212> TYPE: DNA
<213> ORGANISM: Artificial Sequence
<220> FEATURE:
<223> OTHER INFORMATION: Artificial Sequence oligonucleotide

<400> SEQUENCE: 66
gaccaaggtc gtaatagtga ggcttatctg ttctta    36

<210> SEQ ID NO 67
<211> LENGTH: 36
<212> TYPE: DNA
<213> ORGANISM: Artificial Sequence
<220> FEATURE:
<223> OTHER INFORMATION: Artificial Sequence oligonucleotide

```
<400> SEQUENCE: 67
gaccaaggtc gtaatagtcc cgcttatctg ttctta                                36

<210> SEQ ID NO 68
<211> LENGTH: 36
<212> TYPE: DNA
<213> ORGANISM: Artificial Sequence
<220> FEATURE:
<223> OTHER INFORMATION: Artificial Sequence oligonucleotide

<400> SEQUENCE: 68
gaccaaggtc gtaatgcagg cgcttatctg ttctta                                36

<210> SEQ ID NO 69
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n stands for any base"

<400> SEQUENCE: 69
caaggtcgta atcagttann statctgttc ttaccgaat                             39

<210> SEQ ID NO 70
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n stands for any base"

<400> SEQUENCE: 70
ggaaagcttt tacaatctnn scaaggacca aattctgat                             39

<210> SEQ ID NO 71
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (19)..(20)
<223> OTHER INFORMATION: "n stands for any base"

<400> SEQUENCE: 71
caatctgagc aaggaccann stctgatgat gaaattaac                             39

<210> SEQ ID NO 72
<211> LENGTH: 38
<212> TYPE: DNA
<213> ORGANISM: Artificial Sequence
<220> FEATURE:
<223> OTHER INFORMATION: Artificial Sequence oligonucleotide

<400> SEQUENCE: 72
gcttttacaa tctgaccaag gaccaaattc tgatgatg                              38

<210> SEQ ID NO 73
<211> LENGTH: 39
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(22)
<223> OTHER INFORMATION: "n stands for any base"

<400> SEQUENCE: 73
ggcatatatt tgctggccan nngttgcacc gtcatcagc                              39

<210> SEQ ID NO 74
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(22)
<223> OTHER INFORMATION: "n stands for any base"

<400> SEQUENCE: 74
gctgactgat acagcggggn nngtacaaaa agatgatgg                              39

<210> SEQ ID NO 75
<211> LENGTH: 41
<212> TYPE: DNA
<213> ORGANISM: Artificial Sequence
<220> FEATURE:
<223> OTHER INFORMATION: Artificial Sequence oligonucleotide

<400> SEQUENCE: 75
gtgagtgatg ctgttgggca aaatggtttg ttaggttttg c                           41

<210> SEQ ID NO 76
<211> LENGTH: 38
<212> TYPE: DNA
<213> ORGANISM: Artificial Sequence
<220> FEATURE:
<223> OTHER INFORMATION: Artificial Sequence oligonucleotide

<400> SEQUENCE: 76
gaccctactt gtggtgagat tgcatatatt tgctggcc                               38

<210> SEQ ID NO 77
<211> LENGTH: 38
<212> TYPE: DNA
<213> ORGANISM: Artificial Sequence
<220> FEATURE:
<223> OTHER INFORMATION: Artificial Sequence oligonucleotide

<400> SEQUENCE: 77
gaccctactt gtggtgaggt tgcatatatt tgctggcc                               38

<210> SEQ ID NO 78
<211> LENGTH: 38
<212> TYPE: DNA
<213> ORGANISM: Artificial Sequence
<220> FEATURE:
<223> OTHER INFORMATION: Artificial Sequence oligonucleotide

<400> SEQUENCE: 78
gaccctactt gtggtgagcc tgcatatatt tgctggcc                               38

<210> SEQ ID NO 79
```

```
<211> LENGTH: 38
<212> TYPE: DNA
<213> ORGANISM: Artificial Sequence
<220> FEATURE:
<223> OTHER INFORMATION: Artificial Sequence oligonucleotide

<400> SEQUENCE: 79
gaccctactt gtggtgaggc tgcatatatt tgctggcc                              38

<210> SEQ ID NO 80
<211> LENGTH: 34
<212> TYPE: DNA
<213> ORGANISM: Artificial Sequence
<220> FEATURE:
<223> OTHER INFORMATION: Artificial Sequence oligonucleotide

<400> SEQUENCE: 80
gatcatcagg ctggtcgtct cgttattggt ccag                                  34

<210> SEQ ID NO 81
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 81
gaccaaggtc gtaatcagtt actttatctg ttcttaccg                             39

<210> SEQ ID NO 82
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 82
gaccaaggtc gtaatcagtt aatgtatctg ttcttaccg                             39

<210> SEQ ID NO 83
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 83
gaccaaggtc gtaatcagtt aatttatctg ttcttaccg                             39

<210> SEQ ID NO 84
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 84
gaccaaggtc gtaatcagtt attttatctg ttcttaccg                             39

<210> SEQ ID NO 85
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 85
```
gaccaaggtc gtaatgcacc actttatctg ttcttaccg         39

<210> SEQ ID NO 86
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 86
gaccaaggtc gtaatgcacc aatgtatctg ttcttaccg         39

<210> SEQ ID NO 87
<211> LENGTH: 38
<212> TYPE: DNA
<213> ORGANISM: Artificial Sequence
<220> FEATURE:
<223> OTHER INFORMATION: Artificial Sequence oligonucleotide

<400> SEQUENCE: 87
gcttttacaa tctgaccaag gaccaaattc tgatgatg          38

<210> SEQ ID NO 88
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 88
gaccaaggtc gtaatgcgtt agcttatctg ttcttaccg         39

<210> SEQ ID NO 89
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 89
gaccaaggtc gtaatgcggg agcttatctg ttcttaccg         39

<210> SEQ ID NO 90
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 90
gaccaaggtc gtaatgcgtg tgcttatctg ttcttaccg         39

<210> SEQ ID NO 91
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 91
gaccaaggtc gtaatgcgcc agcttatctg ttcttaccg         39

<210> SEQ ID NO 92
<211> LENGTH: 39
<212> TYPE: DNA

```
<213> ORGANISM: Artificial Sequence
<220> FEATURE:
<223> OTHER INFORMATION: Artificial Sequence oligonucleotide

<400> SEQUENCE: 92
gaccaaggtc gtaattcgga agcttatctg ttcttaccg                              39

<210> SEQ ID NO 93
<211> LENGTH: 39
<212> TYPE: DNA
<213> ORGANISM: Artificial Sequence
<220> FEATURE:
<223> OTHER INFORMATION: Artificial Sequence oligonucleotide

<400> SEQUENCE: 93
gaccaaggtc gtaattcgcc agcttatctg ttcttaccg                              39

<210> SEQ ID NO 94
<211> LENGTH: 38
<212> TYPE: DNA
<213> ORGANISM: Artificial Sequence
<220> FEATURE:
<223> OTHER INFORMATION: Artificial Sequence oligonucleotide

<400> SEQUENCE: 94
gcttttacaa tctgaccaag gaccaaattc tgatgatg                               38
```

MODIFIED PYRROLOQUINOLINE QUINONE (PQQ) DEPENDENT GLUCOSE DEHYDROGENASE EXCELLENT IN SUBSTRATE SPECIFICITY

TECHNICAL FIELD

The present invention relates to modified glucose dehydrogenase (also abbreviated as GDH herein) having improved substrate specificity, and particularly relates to modified pyrroloquinoline quinone dependent glucose dehydrogenase (also abbreviated as PQQGDH) using pyrroloquinoline quinone (also abbreviated as PQQ) as a coenzyme, and a method for production thereof and a glucose sensor.

The present invention also relates to a method of enhancing a specific activity of wild type pyrroloquinoline quinone dependent glucose dehydrogenase in an assay system using ferricyanide ion as a mediator.

Furthermore, the present invention relates to modified pyrroloquinoline quinone dependent glucose dehydrogenase having an enhanced specific activity in the assay system using the ferricyanide ion as the mediator, a method for production thereof, and a glucose assay kit and a glucose sensor by the use thereof.

The modified PQQGDH of the present invention is useful for quantitative determination of glucose in clinical laboratory tests and food analyses.

BACKGROUND ART

PQQGDH is glucose dehydrogenase using pyrroloquinoline quinone as a coenzyme, and can be used for assay of blood glucose because it catalyzes a reaction in which glucose is oxidized to produce gluconolactone. A glucose concentration in blood is a very important indicator as an important marker for diabetes in clinical diagnosis. At present, the glucose concentration in blood is primarily measured by a biosensor using glucose oxidase, but some errors have been likely observed in measured values because the reaction is affected by a dissolved oxygen concentration. PQQ dependent glucose dehydrogenase has been noticed as a new enzyme in place of this glucose oxidase.

Our group has found that *Acinetobacter baumannii* NCIMB11517 strain produces PQQ dependent glucose dehydrogenase, cloned a gene thereof and constructed a high expression system thereof (see Patent document 1). PQQ dependent glucose dehydrogenase has had an issue with substrate specificity compared to glucose oxidase

[Patent document 1] JP HEI-11-243949 A Publication

When pyrroloquinoline quinone dependent glucose dehydrogenase is used for the biosensor, the ferricyanide ion is used as the mediator in a common blood glucose monitor. An enzyme is dissolved in blood of a specimen on its strip. The blood has higher viscosity and lower solubility than water and solvents used for other general reagents. Therefore, it is desirable that an amount of the enzyme to be added on the strip is small as the amount of a protein. Thus, it has been desired to acquire pyrroloquinoline quinone dependent glucose dehydrogenase which has an enhanced enzyme activity per unit protein, i.e., an enhanced specific activity.

There has been no report concerning modified pyrroloquinoline quinone dependent glucose dehydrogenase whose specific activity has been enhanced in the assay system using the ferricyanide ion as the mediator.

DISCLOSURE OF THE INVENTION

Figure 1:
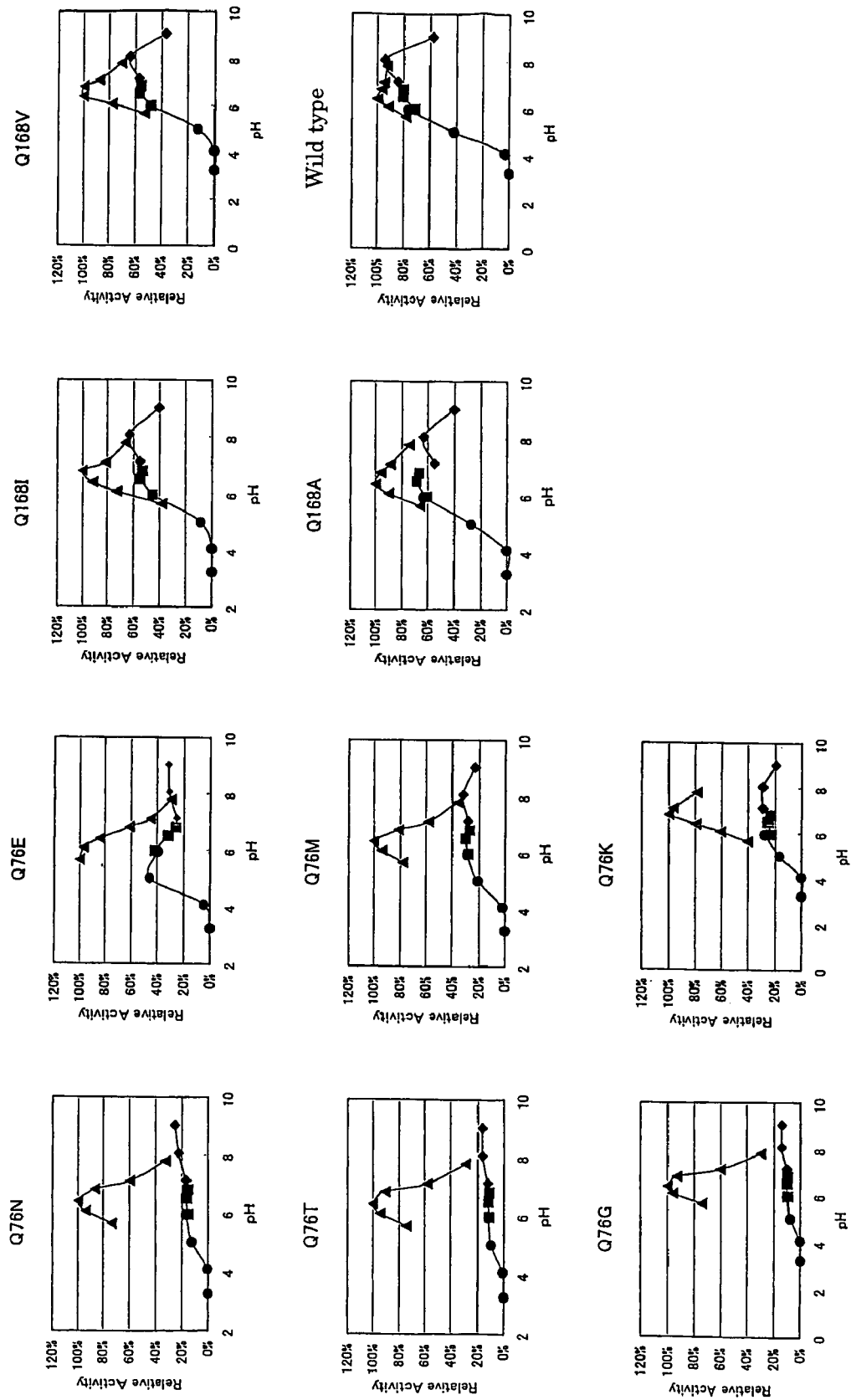
FIG. 1 is a view showing measurement results of optimal pH for Q76N, Q76E, Q168I, Q168V, Q76T, Q76M, Q168A, a wild type, Q76G, and Q76K. A horizontal axis and a vertical axis represent pH and a relative activity, respectively. In the figure, black circles (Acetate) represent the results of measuring an enzyme activity in 50 mM acetate buffer (pH 3.0 to 6.0) containing 0.22% Triton-X100. Likewise, black squares (PIPES) represent the results of measuring the enzyme activity in 50 mM PIPES-NaOH buffer (pH 6.0 to 7.0) containing 0.22% Triton-X100, black triangles (K-PB) represent the results of measuring the enzyme activity in 50 mM phosphate buffer (pH 5.0 to 8.0) containing 0.22% Triton-X100, and black lozenges (Tris-HCl) represent the results of measuring the enzyme activity in 50 mM Tris hydrochloride buffer (pH 7.0 to 9.0) containing 0.22% Triton-X100. A measured value is represented as a relative value with the maximum activity as 100%.

Problems that the Invention is to Solve

The present invention has been made in the context of problems in conventional art, makes a substrate specificity of PQQGDH a problem, and relates to improvement thereof.

The present invention also aims at enhancing a specific activity of pyrroloquinoline quinone dependent glucose dehydrogenase in an assay system using ferricyanide ion as a mediator, compared with a wild type thereof.

Means for Solving the Problems

As a result of an extensive study for solving the above problems, the present inventors have enabled to enhance the substrate specificity by introducing an amino acid mutation into a particular region of PQQGDH.

Furthermore, the present inventors have enabled to enhance the specific activity of pyrroloquinoline quinone dependent glucose dehydrogenase in the assay system using the ferricyanide ion as the mediator, compared with the wild type thereof, by deleting, substituting or adding one or more amino acids in an amino acid sequence of wild type pyrroloquinoline quinone dependent glucose dehydrogenase, and completed the present invention. That is, the present invention relates to:

[Item 1] Modified pyrroloquinoline quinone dependent glucose dehydrogenase (PQQGDH) which has a lower action property on disaccharide than wild type PQQGDH;

[Item 2] The modified pyrroloquinoline quinone dependent glucose dehydrogenase (PQQGDH) according to Item 1, which has more enhanced stability than the wild type PQQGDH;

[Item 3] A method of enhancing a specific activity in an assay system using ferricyanide ion as a mediator compared with a wild type, by deleting, substituting or adding one or more amino acids in an amino acid sequence of the wild type pyrroloquinoline quinone dependent glucose dehydrogenase (PQQGDH);

[Item 4] Modified pyrroloquinoline quinone dependent glucose dehydrogenase (PQQGDH) having a more enhanced specific activity in an assay system using ferricyanide ion as a mediator compared with a wild type by the method according to Item 3;

[Item 5] A gene encoding the modified PQQGDH according to Item 1 or 3;

[Item 6] A vector comprising the gene according to Item 5;

[Item 7] A transformant transformed with the vector according to Item 6;

[Item 8] A method of producing modified PQQGDH characterized by culturing the transformant according to Item 7;

[Item 9] A glucose assay kit comprising the modified PQQGDH according to Item 1 or 3;

[Item 10] A glucose sensor comprising the modified PQQGDH according to Item 1 or 3; and

[Item 11] A method of measuring glucose comprising the modified PQQGDH according to Item 1 or 3.

Effects of the Invention

The modified PQQGDH according to the present invention is an enzyme which has the lower action property on the disaccharide than the wild type PQQGDH. By using the modified PQQGDH according to the present invention for the glucose assay kit and the glucose sensor, it is possible to analyze with higher accuracy and provide the more stable glucose assay kit and glucose sensor compared with a case of using the wild type PQQGDH.

Alternatively, the modified pyrroloquinoline quinone dependent glucose dehydrogenase according to the present invention enables to decrease an amount of the enzyme to be added to the glucose assay kit and the glucose sensor by the use thereof and enables inexpensive production thereof by enhancing the specific activity.

BEST MODE FOR CARRYING OUT THE INVENTION

The present invention will be described below in detail.

The modified PQQGDH of the present invention is an enzyme which has the lower action property on the disaccharide than the wild type PQQGDH.

The action property on the disaccharide means the action to dehydrogenate the disaccharide. As the disaccharides, maltose, sucrose, lactose and cellobiose are exemplified, and in particular, maltose is exemplified. In the present invention, lowering the action property on the disaccharide is also described as enhancement of the substrate specificity.

It is determined as follows whether the action property on the disaccharide is lowered or not.

In an activity assay described in Test Example 1 described later, a PQQGDH activity value (a) using D-glucose as a substrate solution and a PQQGDH activity value (b) using the disaccharide in place of glucose as a substrate solution are measured using the wild type PQQGDH. When the value in the case of using glucose as the substrate is 100, a relative value [(b)/(a)×100] is calculated. Then, the same operation is performed using the modified PQQGDH, and the determination is performed by comparing the values.

If the modified PQQGDH of the present invention has the lower action property on the disaccharide than the wild type PQQGDH, it is included in the modified PQQGDH of the present invention regardless of an increased, unchanged or lowered action property on glucose.

The modified PQQGDH of the present invention includes those having the lower action property on the disaccharide in the measurement of a glucose concentration compared with the case of using the wild type PQQGDH. Those having the lower action property on maltose are preferable. The action property on maltose is preferably 90% or less, more preferably 75% or less, still more preferably 70% or less, still more preferably 60% or less, especially 40% or less and more especially 20% or less of the wild type PQQGDH.

The modified PQQGDH of the present invention includes those where the action property on maltose is 90% or less of the action property on glucose.

The modified PQQGDH of the present invention includes those having a larger Km value for the disaccharide than the wild type PQQGDH. Preferably, the Km value for maltose is large. The Km value for maltose is preferably 8 mM or more, more preferably 12 mM or more and especially 20 mM or more.

The modified PQQGDH of the present invention includes those where the Km value for the disaccharide is larger than the Km value for glucose. Preferably, the km value for maltose is larger than the Km value for glucose. Alternatively, preferably, the Km value for maltose is 1.5 times or larger and more preferably 3 times or larger than the Km value for glucose.

The modified PQQGDH of the present invention is the enzyme having the lower action property on the disaccharide than the wild type PQQGDH, and is desirably the enzyme further having more enhanced stability than the wild type PQQGDH.

The stability (also represented by thermal stability herein) in the present invention is evaluated by a survival rate of the activity after a thermal treatment at 58° C. for 30 minutes. The modified PQQGDH of the present invention includes those where the survival rate of the activity after the thermal treatment at 58° C. for 30 minutes is higher than that in the wild type PQQGDH. The survival rate of the activity is preferably 48% or more, more preferably 55% or more and in particular preferably 70% or more.

As the modified PQQGDH of the present invention having the lower action property on the disaccharide than the wild type PQQGDH, for example, the modified PQQGDH in which an amino acid has been substituted at least at one position selected from the group consisting of positions 170, 245, 249, 349, and 429 in an amino acid sequence of PQQGDH derived from genus *Acinetobacter* is exemplified.

The foregoing amino acid sequence of PQQGDH derived from the genus *Acinetobacter* is preferably an amino acid sequence of PQQGDH derived from *Acinetobacter calcoaceticus* or *Acinetobacter baumannii*. Among others, SEQ ID NO:1 is preferable. The wild type PQQGDH protein represented by SEQ ID NO:1 and a base sequence thereof represented by SEQ ID NO:2 originate from *Acinetobacter baumannii* NCIMB11517 strain, and disclosed in JP HEI-11-243949 A Publication. In the above SEQ ID NO:1, after removing a signal sequence, aspartic acid is numbered as 1 in the amino acid sequence.

The *Acinetobacter baumannii* NCIMB11517 strain was previously classified into *Acinetobacter calcoaceticus*.

In the modified PQQGDH of the present invention, a portion of other amino acid residues may be deleted or substituted, or the other amino acid residue may be added as long as the modified PQQGDH has a glucose dehydrogenase activity, and preferably no substantial adverse effect is given to the action property on the disaccharide and/or the stability.

As the modified PQQGDH of the present invention having the lower action property on the disaccharide than the wild type PQQGDH, for example, the modified PQQGDH which has an amino acid substitution at least at one position of positions 67, 68, 69, 76, 89, 167, 168, 169, 170, 341, 342, 343, 351, 49, 174, 188, 189, 207, 215, 245, 249, 300, 349, 129, 130, 131 and 429, and/or in which an amino acid has been inserted between positions 428 and 429 are exemplified.

As the modified PQQGDH of the present invention having the improved substrate specificity, for example, GDH having the amino acid substitution and GDH in which the amino acid has been inserted between positions 428 and 429 in the amino acid sequence of PQQGDH derived from the genus *Acinetobacter* are exemplified.

The modified PQQGDH which has at least one of the amino acid substitutions selected from the group consisting of Q76N, Q76E, Q76T, Q76M, Q76G, Q76K, N167E, N167L, N167G, N167T, N167S, N167A, N167M, Q168I, Q168V, Q168A, Q168C, Q168D, Q168E, Q168F, Q168G, Q168H, Q168K, Q168L, Q168M, Q168N, Q168R, Q168S, Q168W, L169D, L169S, L169W, L169Y, L169A, L169N, L169M, L169V, L169C, L169Q, L169H, L169F, L169R, L169K, L169I, L169T, L169P, L169G, L169E, A170L, A170I, A170K, A170F, A170W, A170P, A170M, K89E, K300R, S207C, N188I, T349S, K300T, L174F, K49N, S189G, F215Y, S189G, E245D, E245F, E245H, E245M, E245N, E245Q, E245V, E245C, N249G, N249A, N249E, N249Q, A351T, P67K, E68K, P67D, E68T, I69C, P67R, E68R, E129R, K130G, P131G, E129N, P131T, E129Q, K130T, P131R, E129A, K130R, P131K, E341L, M342P, A343R, A343I, E341P, M342V, E341S, M342I, A343C, M342R, A343N, T349S, T349P, T349Y, N429F, N429P, N429L, N429Y, A343N, L169P, L169G and L169E, and/or in which L, A or K has been inserted between positions 428 and 429 are preferable.

The substitution at positions 67, 68, 69, 76, 89, 167, 168, 169, 341, 342, 343, 351, 49, 174, 188, 189, 207, 215, 245, 300, 349, 129, 130, 131 and 429 may be performed at one position or at multiple positions.

Herein, "Q76N" means that Q (Gln) at position 76 is substituted with N (Asn).

Any of the substitutions shown in the following paragraph and/or the insertion of L, A or K between the positions 428 and 429 contribute to enhancement of substrate specificity of PQQGDH.

Q76N, Q76E, Q76T, Q76M, Q76G, Q76K, Q168I, Q168V, Q168A, Q168C, Q168D, Q168E, Q168F, Q168G, Q168H, Q168K, Q168L, Q168M, Q168N, Q168R, Q168S, Q168W, L169A, L169V, L169H, L169K, L169D, L169S, L169N, L169G, L169C, A170L, A170I, A170K, A170F, A170W, A170P, E245F, E245H, E245M, E245N, E245Q, E245V, E245C, N249G, N249A, N249E, N249Q, (Q168A+L169G+E245D), (Q168A+L169P+E245D), (K89E+K300R), (Q168A+L169D), (Q168S+L169S), (N167E+Q168G+L169T), (N167S+Q168N+L169R), (Q168G+L169T), (N167G+Q168S+L169Y), (N167L+Q168S+L169G), (N167G+Q168S+L169S+L174F+K49N), (Q168N+L168N+S189R), (N167E+Q168G+L169A+S189G), (N167G+Q168R+L169A), (N167S+Q168G+L169A), (N167G+Q168V+L169S), (N167S+Q168V+L169S), (N167T+Q168I+L169G), (N167G+Q168W+L169N), (N167G+Q168S+L169N), (N167G+Q168S+L169V), (Q168R+L169C), (N167S+Q168L+L168G), (Q168C+L169S), (N167T+Q168N+L169K), (N167G+Q168T+L169A+S207C), (N167A+Q168A+L169P), (N167G+Q168S+L169G), (N167G+Q168G), (N167G+Q168D+L169K), (Q168P+L169G), (N167G+Q168N+L169S), (Q168S+L169G), (N188I+T349S), (N167G+Q168G+L169A+F215Y), (N167G+Q168T+L169G), (Q168G+L169V), (N167G+Q168V+L169T), (N167E+Q168N+L169A), (Q168R+L169A), (N167G+Q168R), (N167G+Q168T), (N167G+Q168T+L169Q), (Q168I+L169G+K300T), (N167G+Q168A), (N167T+Q168L+L169K), (N167M+Q168Y+L169G), (N167E+Q168S), (N167G+Q168T+L169V+S189G), (N167G+Q168G+L169C), (N167G+Q168K+L169D), (Q168A+L169D), (Q168S+E245D), (Q168S+L169S), (A351T), (N167S+Q168S+L169S), (Q168I+L169Q), (N167A+Q168S+L169S), (Q168S+L169E), (Q168A+L169G), (Q168S+L169P), (P67K+E68K), (P67R+E68R+I69C), (P67D+E68T+I69C), (E129R+K130G+P131G), (E129Q+K130T+P131R), (E129N+P131T), (E129A+K130R+P131K), (E341L+M342P+A343R), (E341S+M342I), A343I, (E341P+M342V+A343C), (E341P+M342V+A343R), (E341L+M342R+A343N), (Q168A+L169A), (Q168A+L169C), (Q168A+L169E), (Q168A+L169F), (Q168A+L169H), (Q168A+L169I), (Q168A+L169K), (Q168A+L169M), (Q168A+L169N), (Q168A+L169P), (Q168A+L169Q), (Q168A+L169R), (Q168A+L169S), (Q168A+L169T), (Q168A+L169V), (Q168A+L169W) and (Q168A+L169Y).

As the PQQGDH of the present invention having the more enhanced thermal stability than the wild type PQQGDH, for example, the modified PQQGDH having the amino acid substitution at least at one position of positions 20, 76, 89, 168, 169, 245, 246 and 300 in the amino acid sequence of PQQGDH derived from the genus *Acinetobacter* is exemplified.

Preferably, the modified PQQGDH has the amino acid substitution selected from the group consisting of K20E, Q76M, Q76G, K89E, Q168A, Q168D, Q168E, Q168F, Q168G, Q168H, Q168M, Q168P, Q168W, Q168Y, Q168S, L169D, L169E, L169P, L169S, Q246H, K300R, Q76N, Q76T, Q76K, L169A, L169C, L169E, L169F, L169H, L169K, L169N, L169Q, L169R, L169T, L169Y and L169G. The substitution at positions 20, 76, 89, 168, 169, 245, 246 and 300 may be performed at one position or multiple positions.

Herein, "K20E" means that K (Lys) at position 20 is substituted with E (Glu).

Any of the amino acid substitutions shown below contribute to the enhancement of the thermal stability of PQQGDH.

In particular, K20E, Q76M, Q76G, (K89E+K300R), Q168A, (Q168A+L169D), (Q168S+L169S), Q246H, Q168D, Q168E, Q168F, Q168G, Q168H, Q168M, Q168P, Q168W, Q168Y, Q168S, (Q168S+L169E), (Q168S+L169P), (Q168A+L169A), (Q168A+L169C), (Q168A+L169E), (Q168A+L169F), (Q168A+L169H), (Q168A+L169K), (Q168A+L169N), (Q168A+L169P), (Q168A+L169Q), (Q168A+L169R), (Q168A+L169T), (Q168A+L169Y), (Q168A+L169G), (Q168A+L169P+E245D) and (Q168A+L169G+E245D).

Alternatively, as the modified PQQGDH of the present invention having the lower action property on the disaccharide than the wild type PQQGDH, for example, the modified PQQGDH having the amino acid substitution at least at one position of positions 74, 146, 168, 169, 170, 245 and 342 in the amino acid sequence of PQQGDH derived from the genus *Acinetobacter* is exemplified.

Among the above, the modified PQQGDH having the amino acid substitution at least at one position of positions 74 and 146 is more preferable. By introducing a mutation to these positions, it is possible to anticipate the enhancement of the specific activity in reactivity to glucose compared with the wild type enzyme in addition to lowering the action property on the disaccharide. It is also likely to enhance the reactivity in a system including a mediator.

The modified PQQGDH having at least one of the amino acid substitutions selected from the group consisting of D74V, S146A, Q168A, L169P, A170L, A170M, A170I, A170F, E245D, M342I, M342V, M342P and M342A is preferable.

Among the above, the modified PQQGDH having the amino acid substitution at least one position of D74V and S146A is more preferable.

Herein, "M342A" means that M (Met) at position 342 is substituted with A (Ala).

Any of the substitutions shown in the following paragraph contribute to the enhancement of the substrate specificity of PQQGDH.

D74V, M342I, M342V, M342P, M342A, S146A, Q168A, L169P, A170L, A170M, A170I, A170F, (S146A+A170L), (Q168A+L169P+A170L), (S146A+A170M), (Q168A+L169P+A170M), (S146A+Q168A+L169P+A170L), (S146A+Q168A+L169P+A170M), (Q168A+L169P+A170L+E245D), (Q168A+L169P+A170M+E245D), (S146A+M342I), (Q168A+L169P+A170L+M342I), (Q168A+L169P+A170M+M342I), (S146A+M342V), (Q168A+L169P+A170L+M342V), (Q168A+L169P+A170M+M342V), (S146A+M342P), (Q168A+L169P+A170L+M342P), (Q168A+L169P+A170M+M342P), (S146A+M342A), (Q168A+L169P+A170L+M342A), (Q168A+L169P+A170M+M342A), (D74V+S146A), (D74V+Q168A+L169P+A170L), (D74V+Q168A+L169P+A170M), (Q168A+L169P+A170L+E245D+M342I), (Q168A+L169P+A170M+E245D+M342I), (Q168A+L169P+A170L+E245D+M342V), (Q168A+L169P+A170M+E245D+M342V), (Q168A+L169P+A170L+E245D+M342) and (Q168A+L169P+A170M+E245D+M342A).

Among the above, the modified PQQGDH having the amino acid substitution at least one position of D74V and S146A is more preferable.

Among the above, as another embodiment of the modified PQQGDH of the present invention, more preferably, the modified PQQGDH in which the amino acid substitution is selected from the group consisting of A170V, A170L, A170I, A170T, A170K, A170C, A170M, A170F, A170Y, A170W, A170P, E245D, E245F, E245H, E245M, E245N, E245Q, E245S, E245T, E245V, E245W, E245R, E245G, E245C, N249G, N249A, N249L, N249E, N249Q, T349S, T349P, T349Y, N429F, N429P, N429L and N429Y is exemplified.

Alternatively, as another embodiment of the modified PQQGDH of the present invention, preferably, the modified PQQGDH in which the amino acid substitution is selected from the group consisting of (Q168A+L169G+E245D), (Q168A+L169P+E245D), (S146A+A170L), (Q168A+L169P+A170L), (S146A+A170M), (Q168A+L169P+A170M), (S146A+Q168A+L169P+A170L), (S146A+Q168A+L169P+A170M), (Q168A+L169P+A170L+E245D), (Q168A+L169P+A170M+E245D), (S146A+M342I), (Q168A+L169P+A170L+M342I), (Q168A+L169P+A170M+M342I), (S146A+M342V), (Q168A+L169P+A170L+M342V), (Q168A+L169P+A170M+M342V), (S146A+M342P), (Q168A+L169P+A170L+M342P), (Q168A+L169P+A170M+M342P), (S146A+M342A), (Q168A+L169P+A170L+M342A), (Q168A+L169P+A170M+M342A), (D74V+S146A), (D74V+Q168A+L169P+A170L), (D74V+Q168A+L169P+A170M), (Q168A+L169P+A170L+E245D+M342I), (Q168A+L169P+A170M+E245D+M342I), (Q168A+L169P+A170L+E245D+M342V), (Q168A+L169P+A170M+E245D+M342V), (Q168A+L169P+A170L+E245D+M342A) and (Q168A+L169P+A170M+E245D+M342A) is exemplified.

More preferably, (Q168A+L169P+A170L+E245D+M342I) and (Q168A+L169P+E245D) are included. These are preferable because they not only have the low action property on the disaccharide but also are excellent in thermal stability.

The method of enhancing the specific activity in the assay system using the ferricyanide ion as the mediator of the present invention can be accomplished by deleting, substituting or adding one or more amino acids in the amino acid sequence of the wild type pyrroloquinoline quinone dependent glucose dehydrogenase (also referred to as PQQGDH herein). The wild type PQQGDH which is a source of the modification is the enzyme which coordinates pyrroloquinoline quinone as the coenzyme and catalyzes the reaction in which D-glucose is oxidized to produce D-glucono-1,5-lactone, and its origin and structure are not especially limited.

Representative origins of the wild type PQQGDH which is the source of the modification are microorganisms exemplified below. Specifically, examples may include oxidizing bacteria such as *Acinetobacter calcoaceticus, Acinetobacter baumannii, Pseudomonas aeruginosa, Pseudomonas putida, Pseudomonas fluorescens* and *Gluconobacter oxydans*, and enterobacteria such as *Agrobacterium radiobacter, Escherichia coli* and *Klebsiella aerogenes*. But, it is difficult to modify a membrane type enzyme present in *Escherichia coli* to make a soluble type, and it is preferable to select those derived from the microorganisms belonging to the genus *Acinetobacter* as the origin. More preferably, it is preferable to select the soluble PQQGDH from *Acinetobacter calcoaceticus* or *Acinetobacter baumannii*.

The amino acid sequence of the above PQQGDH derived from the genus *Acinetobacter* is preferably the amino acid sequence of PQQGDH derived from *Acinetobacter calcoaceticus* or *Acinetobacter baumannii*. Among others, it is preferably SEQ ID NO:1. The wild type PQQGDH protein represented by SEQ ID NO:1 and the base sequence thereof represented by SEQ ID NO:2 originate from *Acinetobacter baumannii* NCIMB11517 strain, and disclosed in JP HEI-11-243949 A Publication. In the above SEQ ID NO:1, after removing the signal sequence, aspartic acid is numbered as 1 in the amino acid sequence.

The *Acinetobacter baumannii* NCIMB11517 strain was previously classified into *Acinetobacter calcoaceticus*.

The specific activity in the present invention is the activity per oxygen molecules of a unit weight in the activity assay system using the ferricyanide ion as the mediator, and more particularly, is the unit of the enzyme activity per 1 mg of the purified enzyme.

An active center in the present invention refers to a site receiving catalysis by binding D-glucose which is the substrate in pyrroloquinoline quinone dependent glucose dehydrogenase, and is composed of a substrate-binding site at which D-glucose is bound and a pyrroloquinone-binding site at which a catalytic oxidation reaction is performed.

The wild type pyrroloquinoline quinone dependent glucose dehydrogenase in the present invention is naturally occurring pyrroloquinoline quinone dependent glucose dehydrogenase. Meanwhile, the modified pyrroloquinoline quinone dependent glucose dehydrogenase has one or more amino acid deletions, substitutions or insertions in its amino acid sequence compared with the wild type pyrroloquinoline quinone dependent glucose dehydrogenase.

The enhancement of the specific activity in the present invention generally includes 10% or more enhancement of the specific activity compared with the wild type, and the enhancement is preferably 50% or more compared with the wild type.

The modified PQQGDH having the more enhanced specific activity than the wild type PQQGDH in the assay system using the ferricyanide ion as the mediator, for example, includes the modified pyrroloquinoline quinone dependent glucose dehydrogenase having the more enhanced specific activity than the wild type PQQGDH in the assay system using the ferricyanide ion as the mediator by substituting at least one amino acid in the vicinity of the active center with another amino acid.

The modified PQQGDH of the present invention having the more enhanced specific activity than the wild type PQQGDH in the assay system using the ferricyanide ion as the mediator is more particularly one in which at least one amino acid present within a radius of 10 angstroms from the active center has been substituted with another amino acid. That amino acid is composed of the amino acids at positions selected from the group consisting of positions 76, 143, 144, 163, 168, 169, 228, 229, 247, 248, 343, 346, 348, 377, 406, 408 and 424 in the amino acid sequence of PQQGDH derived from the genus *Acinetobacter*.

Also, as PQQGDH of the present invention, the modified pyrroloquinoline quinone dependent glucose dehydrogenase having the amino acid substitution at least at one position of the positions 168 and 169 in the amino acid sequence of PQQGDH derived from the genus *Acinetobacter* is exemplified.

If the PQQGDH of the present invention is more particularly exemplified, pyrroloquinoline quinone dependent glucose dehydrogenase having the amino acid substitution selected from the group consisting of Q168A, (Q168A+L169G), (Q168A+L169C), (Q168A+L169P), (Q168S+L169E) and (Q168S+L169P) in the amino acid sequence of PQQGDH derived from the genus *Acinetobacter* is exemplified.

Herein, Q168A means that Q (Gln) at position 168 is substituted with A (Ala).

In the modified PQQGDH of the present invention, a portion of other amino acid residues may be deleted or substituted, or the other amino acid residue may be added as long as the modified PQQGDH has the glucose dehydrogenase activity, and preferably no substantial adverse effect is given to the specific activity in the assay system using the ferricyanide ion as the mediator.

The PQQGDH of the present invention is also the modified pyrroloquinoline quinone dependent glucose dehydrogenase in which the enhancement of the specific activity is kept in the assay system using the ferricyanide ion as the mediator compared with the wild type even when the amino acid substitution not close to the active center has been added to the above amino acid substitution.

Particularly, it is the modified pyrroloquinoline quinone dependent glucose dehydrogenase in which the amino acid substitution at position 245 has been combined, and more particularly it is the modified pyrroloquinoline quinone dependent glucose dehydrogenase having the amino acid substitution selected from the group consisting of (Q168A+L169G+E245D) and (Q168A+L169P+E245D).

The method of enhancing the specific activity of pyrroloquinoline quinone dependent glucose dehydrogenase in the assay system using ferricyanide ion as the mediator of the present invention than the wild type can be accomplished by deleting, substituting or adding one or more amino acids in the amino acid sequence of the enzyme.

In the method of the present invention, the deleted, substituted or added amino acid is not especially limited, but is desirably the amino acid in the vicinity of the active center. Alternatively, it is desirable that the deleted, substituted or added amino acid is present within a radius of 10 angstroms from the active center.

In the method of the present invention, it is desirable that at least one amino acid at the position selected from the group consisting of the positions 76, 143, 144, 163, 168, 169, 228, 229, 247, 248, 343, 346, 348, 377, 406, 408 and 424 has been substituted with another amino acid in the amino acid sequence of pyrroloquinoline quinone dependent glucose dehydrogenase derived from the genus *Acinetobacter*.

It is also desirable that at least one amino acid at the position selected from the group consisting of the positions 168 and 169 has been substituted with another amino acid in the amino acid sequence of PQQGDH derived from the genus *Acinetobacter*.

Furthermore, it is desirable that the amino acid substitution is selected from the group consisting of Q168A, (Q168A+L169G), (Q168A+L169C), (Q168A+L169P), (Q168S+L169E) and (Q168S+L169P) in the amino acid sequence of PQQGDH derived from the genus *Acinetobacter*.

The amino acid substitution not close to the active center may be added to the above amino acid substitution, and at that time, the substituted amino acid is desirably the amino acid at position 245 in the amino acid sequence of PQQGDH derived from the genus *Acinetobacter*. Furthermore, it is desirable that the substitution is selected from the group consisting of (Q168A+L169G+E245D) and (Q168A+L169P+E245D).

Upon filing the present invention, the result of X-ray crystal structure analysis of the enzyme derived from *Acinetobacter calcoaceticus* LMD79.41 strain was reported, and the conformational structure of the enzyme including the active center has been demonstrated (see Non-patent documents 1, 2, 3 and 4).

[Non-patent document 1] J. Mol. Biol., 289, 319-333 (1999)
[Non-patent document 2] PNAS, 96(21), 11787-11791 (1999)
[Non-patent document 3] The EMBO Journal, 18(19), 5187-5194 (1999)
[Non-patent document 4] Protein Science, 9, 1265-1273 (2000)

Study on correlation of the structure and the function of the enzyme has been carried forward on the basis of the findings for the conformational structure, but it can not be said yet that the correlation has been completely demonstrated. For example, it has been discussed that selectivity for glucose can be improved by introducing a mutation into a particular site of a structural gene for amino acid residues in a loop region (W6BC) which links B strand and C strand of the 6th W-motif in water-soluble glucose dehydrogenase (e.g., see Patent document 2), however, the effect has been demonstrated only in Example disclosed.

[Patent document 2] JP 2001-197888 A

Herein, reviewing these findings for the conformational structure based on the results of the present invention, it is likely that at least one or more of the amino acids involved in binding of PQQ and/or the amino acids in the vicinity thereof, the amino acids involved in binding of glucose and/or the amino acids in the vicinity thereof and the amino acids involved in binding of calcium ion and/or the amino acids in the vicinity thereof are involved in the modification of the action property on the disaccharide.

The modified PQQGDH of the present invention includes those in which the amino acid involved in binding of PQQ and/or the amino acid in the vicinity thereof, and/or the amino acid involved in binding of glucose and/or the amino acid in the vicinity thereof have been substituted in PQQ dependent glucose dehydrogenase derived from the genus *Acinetobacter*, e.g., PQQ dependent glucose dehydrogenase described in SEQ ID NO:1. In Non-patent documents 3 and 4, it is described that the amino acids involved in binding of PQQ include Y344, W346, R228, N229, K377, R406, R408 and D424 and the amino acids involved in binding of glucose include Q76, D143, H144, D163, Q168 and L16.

The modified PQQGDH of the present invention includes those in which the amino acid involved in binding of calcium ion and/or the amino acid in the vicinity thereof have been substituted in PQQ dependent glucose dehydrogenase derived from the genus *Acinetobacter*, e.g., PQQ dependent glucose dehydrogenase described in SEQ ID NO:1. In Non-patent document 1, it is described that the amino acids involved in binding of calcium ion include P248, G247, Q246, D252 and T348.

The modified PQQGDH of the present invention also includes those obtained by mutating the amino acid located within a radius of 15 angstroms, preferably a radius of 10 angstroms from the active center in the active three dimensional structure of the wild type enzyme.

The modified PQQGDH of the present invention also includes those obtained by mutating the amino acid located within a radius of 10 angstroms from the substrate in the active three dimensional structure of the wild type enzyme. In particular, when the substrate is glucose, those obtained by mutating the amino acid located within a radius of 10 angstroms from the substrate in the active three dimensional structure of the wild type enzyme are preferable.

The modified PQQGDH of the present invention also includes those obtained by mutating the amino acid located within a radius of 10 angstroms from an OH group which binds to a carbon at position 1 of the substrate in the active three dimensional structure of the wild type enzyme. In particular, when the substrate is glucose, those obtained by mutating the amino acid located within a radius of 10 angstroms from the substrate in the active three dimensional structure of the wild type enzyme are preferable.

The modified PQQGDH of the present invention also includes those obtained by mutating the amino acid located within a radius of 10 angstroms from the OH group which binds to the carbon at position 2 of the substrate in the active three dimensional structure of the wild type enzyme. In particular, when the substrate is glucose, those obtained by mutating the amino acid located within a radius of 10 angstroms from the substrate in the active three dimensional structure of the wild type enzyme are preferable.

According to the above teachings, with reference to the wild type PQQGDH protein represented by SEQ ID NO:1 originating from *Acinetobacter baumannii* NCIMB11517 and the base sequence thereof represented by SEQ ID NO:2, those skilled in the art can obtain the modified PQQGDH having the lower action property on the disaccharide than the wild type PQQGDH by substituting the amino acid residue in the region without excessive trials and errors for the modified PQQGDH derived from the other origins (regardless of natural, modified and artificially synthesized ones) with high homology thereto (having preferably 80% or more and more preferably 90% or more homology).

Alternatively, reviewing these findings for the conformational structure from another standpoint based on the results of the present invention, it is thought that the substitution of one or more amino acid residues in the vicinity of the active center is involved in the enhancement of the specific activity in the assay system using the ferricyanide ion as the mediator.

In the present invention, the amino acids in the vicinity of the active center indicate the amino acids involved in binding to PQQ, glucose and/or calcium ion coordinating to PQQ, and the region other than this is referred to as non-vicinity of the active center.

The modified PQQGDH of the present invention also includes those obtained by mutating the amino acid located within a radius of 10 angstroms from the active three dimensional structure of the wild type enzyme.

The modified PQQGDH of the present invention also substantially includes those obtained by mutating the amino acid located within a radius of 10 angstroms from the substrate in the active three dimensional structure of the wild type enzyme. In particular, when the substrate is glucose, those obtained by mutating the amino acid located within a radius of 10 angstroms from the substrate in the active three dimensional structure of the wild type enzyme are preferable.

The modified PQQGDH of the present invention also substantially includes those obtained by mutating the amino acid located within a radius of 10 angstroms from the OH group which binds to the carbon at position 1 of the substrate in the active three dimensional structure of the wild type enzyme. In particular, when the substrate is glucose, those obtained by mutating the amino acid located within a radius of 10 angstroms from the substrate in the active three dimensional structure of the wild type enzyme are preferable.

The modified PQQGDH of the present invention also substantially includes those obtained by mutating the amino acid located within a radius of 10 angstroms from the OH group which binds to the carbon at position 2 of the substrate in the active three dimensional structure of the wild type enzyme. In particular, when the substrate is glucose, those obtained by mutating the amino acid located within a radius of 10 angstroms from the substrate in the active three dimensional structure of the wild type enzyme are preferable.

When the modification is performed at multiple positions, if the specific activity is enhanced in the assay system using the ferricyanide ion as the mediator when the modified PQQGDH as a total is compared with the wild type, it is not necessary that all modified positions are present in the vicinity of the active center.

According to the above teachings, those skilled in the art can obtain the modified PQQGDH having the more enhanced specific activity in the assay system using the ferricyanide ion as the mediator than the wild type PQQGDH by substituting the amino acid residue in the region for the modified PQQGDH derived from the other origins.

For example, when the amino acid sequence in SEQ ID NO:1 is compared with the amino acid sequence of the enzyme derived from *Acinetobacter calcoaceticus* LMD79.41 strain, a few sites are different and the homology (including the signal sequence) is 92.3%. Thus, since they are very similar, it can be easily recognized what amino acid residue in the enzyme from the other origin a certain residue in SEQ ID NO:1 corresponds to. And, according to the present invention, the modified PQQGDH having the lower action property on the disaccharide than the wild type PQQGDH can be obtained by deleting, substituting or inserting the amino acids at such one or more sites. These modified PQQGDH are also included within the scope of the present invention.

The present invention is a gene encoding the above modified pyrroloquinoline quinone dependent glucose dehydrogenase.

The present invention is a gene encoding the modified pyrroloquinoline quinone dependent glucose dehydrogenase (PQQGDH) having the lower action property on the disaccharide than the wild type PQQGDH. The invention is further a vector comprising the gene, is further a transformant transformed with the vector, and is further a method of producing the modified PQQGDH characterized in that the transformant is cultured.

The gene encoding the modified PQQGDH of the present invention is likely obtained by modifying a DNA fragment comprising a gene encoding the wild type PQQGDH obtained from various origins such as microorganisms. Specifically, examples of the microorganisms can include oxidizing bacteria such as *Acinetobacter calcoaceticus, Acinetobacter baumannii, Pseudomonas aeruginosa, Pseudomonas putida, Pseudomonas fluorescens* and *Gluconobacter oxydans*, and enterobacteria such as *Agrobacterium radiobacter, Escherichia coli* and *Klebsiella aerogenes*. But, it is difficult to modify the membrane type enzyme present in *Escherichia coli* to make the soluble type, and it is preferable to select those derived from the microorganisms belonging to the genus *Acinetobacter* as the origin. More preferably, it is preferable to select the soluble PQQGDH from either *Acinetobacter calcoaceticus* or *Acinetobacter baumannii* with high homology.

As the method of modifying the gene encoding the wild type PQQGDH, techniques usually performed to modify genetic information are used. That is, a DNA having the genetic information of the modified protein is made by converting a particular base or by inserting or deleting a particular base in a DNA having the genetic information of the protein. Examples of specific methods to convert the base in the DNA include use of commercially available kits (Transformer Mutagenesis Kit supplied from Clonetech; EXOIII/Mung Bean Deletion Kit supplied from Stratagene; QuickChange Site Directed Mutagenesis Kit supplied from Stratagene), or utilization of a polymerase chain reaction (PCR) method.

The produced DNA having the genetic information of the modified protein is transferred in a state ligated with a plasmid into a host microorganism, which will become a transformant producing the modified protein. As the plasmid in this case, pBluescript, pUC18 and the like can be utilized when using *Escherichia coli* as the host microorganism. As the host microorganism, *Escherichia coli* W3110, *Escherichia coli* C600, *Escherichia coli* JM109, *Escherichia coli* DH5α and the like can be utilized. As the method of transfecting a recombinant vector into the host microorganism, for example, when the host microorganism belongs to the genus *Escherichia*, the method of transfecting the recombinant DNA in the presence of calcium ion can be employed, and further an electroporation method may be used. In addition, commercially available competent cells (e.g., Competent High JM109 supplied from Toyobo) may also be used.

Such a gene may be extracted from these bacterial strains, or can be chemically synthesized. Furthermore, it is also possible to obtain a DNA fragment containing a PQQGDH gene by utilizing the PCR method.

The method of obtaining the gene encoding PQQGDH in the present invention includes the following methods. For example, chromosomes of *Acinetobacter calcoaceticus* NCIB11517 strain are separated and purified. Subsequently, a DNA fragment cleaved using sonication and restriction enzyme digestion and a linear expression vector are bound and closed in blunt ends or cohesive ends of the both DNA using DNA ligase to construct a recombinant vector. The recombinant vector is transfected into a replicable host microorganism. Then, the microorganism retaining the recombinant vector containing the gene encoding GDH with PQQ as a prosthetic group is obtained by screening using the expression of a marker in the vector and the enzyme activity as indicators.

Then, the microorganism retaining the above recombinant vector is cultured, the recombinant vector is separated from microbial cells of the cultured microorganism and is purified, and the gene encoding GDH can be collected from the expression vector. For example, the chromosomal DNA of *Acinetobacter calcoaceticus* NCIB11517 strain which is a gene donor is specifically collected as follows.

The gene donor microorganism is cultured with stirring for 1 to 3 days, and the microbial cells are collected by centrifuging the resulting culture solution. Then, the microbial cells are lysed to prepare a bacteriolysis solution containing the GDH gene with PQQ as the prosthetic group. As the method for bacteriolysis, for example, a treatment with a bacteriolytic enzyme such as lysozyme is given, and if necessary, protease, other enzymes and a surfactant such as sodium lauryl sulfate (SDS) are combined. Physical disruption methods such as freezing and drying, and French press treatment may be combined.

The DNA is separated and purified from the bacteriolysis solution obtained above in accordance with standard methods, for example by optionally combining a deproteinizing treatment such as phenol treatment and protease treatment, ribonuclease treatment, alcohol precipitation treatment and the like.

The DNA separated from the microorganism and purified can be cleaved by, for example, the sonication and the restriction enzyme digestion. Preferably, II type restriction enzymes which act upon a particular nucleotide sequence are suitable.

For the vector upon cloning, phages which can autonomously grow in the host microorganism or those constructed from the plasmid for gene recombination are suitable. As the phage, when *Escherichia coli* is used as the host microorganism, Lambda gt10 and Lambda gt11 are exemplified. As the plasmid, when *Escherichia coli* is used as the host microorganism, pBR322, pUC19 and pBluescript are exemplified.

Upon cloning, the vector as the above can be cleaved with the same restriction enzymes as those used for cleavage of the microbial DNA which is the donor of the gene encoding GDH to yield vector fragments, but it is not always required to use the same restriction enzyme as the restriction enzyme used for the cleavage of the microbial DNA. The method of ligating the microbial DNA fragment and the vector DNA fragment may be the method of using DNA ligase known publicly. For example, after annealing of the cohesive end of the microbial DNA fragment with the cohesive end of the vector DNA fragment, the recombinant vector of the microbial DNA fragment and the vector DNA fragment is made by the use of appropriate DNA ligase. If necessary, after annealing, the DNA fragments can also be transfected into the host microorganism to make the recombinant vector by utilizing in vivo DNA ligase.

The host microorganism is not especially limited as long as the recombinant vector is stable, and can autonomously grow and express a character of an exogenous gene. Generally, *Escherichia coli* W3110, *Escherichia coli* C600, *Escherichia coli* HB101, *Escherichia coli* JM109, *Escherichia coli* DH5 α and the like can be used.

As the method of transfecting the recombinant vector into the host microorganism, for example when the host microorganism is *Escherichia coli*, a competent cell method by calcium treatment, the electroporation method and the like can be used.

The microorganism which is the transformant obtained above can be stably produce GDH in a large amount by being cultured in a nutrient medium. To select the host microorganisms with or without transfection of the objective recombinant vector, the microorganism may be searched which simultaneously expresses a drug resistant marker in the vector keeping the objective DNA and the GDH activity induced by the addition of PQQ. For example, the microorganism may be grown in a selective medium based on the drug resistant marker, and the microorganism which produces GDH may be selected.

The base sequence of the GDH gene with PQQ as the prosthetic group obtained by the above method was decoded by a dideoxy method described in Science 214:1205, 1981. The amino acid sequence of GDH was deduced from the base sequence determined above.

The transfer from the once selected recombinant vector containing the GDH gene with PQQ as the prosthetic group into the recombinant vector replicable in the microorganism having a PQQ production ability can be easily carried out by collecting the DNA which is the GDH gene from the recombinant vector keeping the GDH gene by the restriction enzymes and the PCR method, and ligating the GDH gene to the other vector fragment. The transformation of the microorganism having the PQQ production ability with these vectors can be carried out by the use of the competent cell method by calcium treatment or the electroporation method.

The microorganisms having the PQQ production ability can include methanol assimilating bacteria such as bacteria belonging to the genus *Methylobacterium*, acetic acid bacteria such as bacteria belonging to the genera *Acetobacter* and *Gluconobacter*, and other bacteria such as bacteria belonging to the genera *Flavobacterium*, *Pseudomonas* and *Acinetobacter*. Among others, the bacteria belonging to the genera *Pseudomonas* and *Acinetobacter* are preferable because a usable host-vector system has been established and is easily utilized.

As the bacteria belonging to the genus *Pseudomonas*, *Pseudomonas aeruginosa*, *Pseudomonas fluorescens*, and *Pseudomonas putida* can be used. As the bacteria belonging to the genus *Acinetobacter*, *Acinetobacter calcoaceticus* and *Acinetobacter baumannii* can be used.

As the recombinant vector replicable in the above microorganisms, the vector derived from RSF1010 or the vector having a similar replicon thereto is usable for the bacteria belonging to the genus *Pseudomonas*. For example, pKT240, pMMB24 (M. M. Bagdasarian et al., Gene, 26, 273 (1983)), pCN40, pCN60 (C. C. Nieto et al., Gene, 87, 145 (1990)), and pTS1137 can be included. Also, pME290 (Y. Itoh et al., Gene, 36, 27 (1985)), pNI111, pNI20C (N. Itoh et al., J. Biochem., 110, 614 (1991) can be utilized.

For the bacteria belonging to the genus *Acinetobacter*, pWM43. (W. Minas et al., Appl. Environ. Microbiol., 59, 2807 (1993)), pKT230, pWH1266 (M. Hunger et al., Gene, 87, 45 (1990)) can be utilized as the vector.

The microorganism which is the transformant obtained above can be stably produce the modified protein in a large amount by being cultured in the nutrient medium. As a culture form of the host microorganism which is the transformant, a culture condition may be selected in consideration of nutrient physical nature of the host, and a liquid culture is performed in many cases. Industrially, it is advantageous to perform an aeration stirring culture.

As nutrient sources of the medium, those usually used for the culture of the microorganism are widely used. Carbon sources may be carbon compounds capable of being assimilated, and for example, glucose, sucrose, lactose, maltose, molasses, pyruvic acid and the like are used. Nitrogen sources may be nitrogen compounds capable of being utilized, and for example, peptone, meat extract, yeast extract, hydrolyzed casein, bean cake extracted with alkali and the like are used. Additionally, phosphate salts, carbonate salts, sulfate salts, salts of magnesium, calcium, potassium, manganese and zinc, particular amino acids, particular vitamins, and the like are used as needed.

A culture temperature can be optionally changed in a range in which the bacteria grow and produce the modified PQQGDH, and in the case of the above microorganism having the PQQ production ability, the temperature is preferably about 20 to 42° C. A culture time period is slightly different depending on the condition, and the culture may be completed at an appropriate time period by appropriately selecting the time period when the modified PQQGDH attains to a maximum yield. Typically, the time period is about 6 to 48 hours. A pH value of the medium can be optionally changed in the range in which the bacteria grow and produce the modified PQQGDH, and preferably is in the range of about pH 6.0 to 9.0.

The culture solution containing the microbial cells which produce the modified PQQGDH in the culture can also be directly collected and utilized, but generally in accordance with the standard methods, when the modified PQQGDH is present in the culture solution, the solution containing the modified PQQGDH and the microbial cells are separated by filtration or centrifugation, and then utilized. When the modified PQQGDH is present in the microbial cells, the microbial cells are collected from the resulting culture by a procedure such as filtration and centrifugation, then the microbial cells are disrupted by a mechanical method or an enzymatic method such as lysozyme, and if necessary GDH is solubilized by adding a chelating agent such as EDTA and a surfactant to separate and collect as an aqueous solution.

The solution containing GDH obtained above may be precipitated by, for example, concentration under reduced pressure, membrane concentration, salting out treatment with ammonium sulfate or sodium sulfate, or fractional precipitation with a hydrophilic organic solvent such as methanol, ethanol and acetone. Also, heating treatment and isoelectric point treatment are effective purification procedures. Subsequently, the purified GDH can be obtained by performing gel filtration by an absorbing agent or a gel filtrating agent, absorption chromatography, ion-exchange chromatography or affinity chromatography.

For example, it is possible to separate and purify by the gel filtration using Sephadex gel (Pharmacia Biotech) or column chromatography using DEAE Sepharose CL-6B (Pharmacia Biotech) and octyl Sepharose CL-6B (Pharmacia Biotech) and obtain a purified enzyme preparation. It is preferable that the purified enzyme preparation is purified to an extent that a single band is displayed on electrophoresis (SDS-PAGE).

It is possible to distribute by making the purified enzyme obtained above into powder by freezing and drying, vacuum drying or spray drying. At that time, the purified enzyme can be used by dissolved in phosphate buffer, Tris hydrochloride buffer or Good's buffer. The Good's buffer is suitable, and among others, PIPES, MES or MOPS buffer is preferable. GDH can be further stabilized by adding calcium ion or a salt thereof, and amino acids such as glutamic acid, glutamine and lysine, and serum albumin.

The method of producing the modified protein of the present invention is not especially limited, and it is possible to produce by the procedure shown below. To modify the amino acid sequence which configures the protein, the technique usually performed to modify the genetic information is used. That is, a DNA having the genetic information of the modified protein is made by converting the particular base or by inserting or deleting the particular base in the DNA having the genetic information of the protein. Examples of specific methods to convert the base in the DNA include use of commercially available kits (Transformer Mutagenesis Kit supplied from Clonetech; EXOIII/Mung Bean Deletion Kit supplied from Stratagene; QuickChange Site Directed Mutagenesis Kit supplied from Stratagene), or utilization of the polymerase chain reaction (PCR) method.

In the present invention, the positions 76, 167, 168, 170 and 245 of PQQGDH represented by SEQ ID NO:1 were focused, amino acid substitutions thereof were made, and consequently the modified PQQGDH in which the substrate specificity had been improved could be obtained. Concerning the substrate specificity, Q76K, Q168A, A170P, E245D, (Q168A+L169G+E2 45D), (Q168A+L169P+E245D), (Q168S+L169S), (Q168A+L169D), (Q168S+E245D), (Q168S+L169E), (Q168A+L169G), (Q168S+L169P), (Q168A+L169A), (Q168A+L169C), (Q168A+L169E), (Q168A+L169K), (Q168A+L169M), (Q168A+L169N), (Q168A+L169P), (Q168A+L169S) and (Q168A+L169T) are especially preferable.

In the present invention, the positions 20, 76, 89, 168, 169, 245, 246 and 300 of PQQGDH represented by SEQ ID NO:1 were focused, amino acid substitutions thereof were made, and consequently the modified PQQGDH in which the stability had been improved could be obtained. So far as the thermal stability is concerned, the substitutions of K20E, (K89E+K300R), Q168A, (Q168A+L169D), (Q168S+L169S), (Q168S+L169E), (Q168S+L169P), (Q168A+L169G), Q168D, Q168E, Q168F, Q168G, Q168H, Q168M, Q168P, Q168S, Q168W, Q168Y, (Q168A+L169A), (Q168A+L169C), (Q168A+L169E), (Q168A+L169F), (Q168A+L169H), (Q168A+L169K), (Q168A+L169N), (Q168A+L169P), (Q168A+L169Q), (Q168A+L169R), (Q168A+L169T), (Q168A+L169Y), (Q168A+L169G+E245D), (Q168A+L169P+E245D) and Q246H are especially desirable.

Alternatively, in the present invention, the positions 74, 146, 168, 169, 170, 245 and 342 of PQQGDH represented by SEQ ID NO:1 were focused, amino acid substitutions thereof were made, and consequently the modified PQQGDH in which the substrate specificity had been improved could be obtained. Concerning the substrate specificity, (Q168A+L169P+A170L), (S146A+A170M), (Q168A+L169P+A170M), (S146A+Q168A+L169P+A170L), (S146A+Q168A+L169P+A170M), (Q168A+L169P+A170L+E245D), (Q168A+L169P+A170M+E245D), (S146A+M342I), (Q168A+L169P+A170L+M342I), (Q168A+L169P+A170M+M342I), (S146A+M342V), (Q168A+L169P+A170L+M342V), (Q168A+L169P+A170M+M342V), (S146A+M342P), (Q168A+L169P+A170L+M342P), (Q168A+L169P+A170M+M342P), (S146A+M342A), (Q168A+L169P+A170L+M342A), (Q168A+L169P+A170M+M342A), (D74V+S146A), (D74V+Q168A+L169P+A170L), (D74V+Q168A+L169P+A170M), (Q168A+L169P+A170L+E245D+M342I), (Q168A+L169P+A170M+E245D+M342I), (Q168A+L169P+A170L+E245D+M342V), (Q168A+L169P+A170M+E245D+M342V), (Q168A+L169P+A170L+E245D+M342A), and (Q168A+L169P+A170M+E245D+M342A) are especially preferable.

The modified protein can take various forms such as liquid (aqueous solution, suspension), powder and freezing and drying. The freezing and drying method is not especially limited, and may be performed in accordance with the standard method. A composition comprising the enzyme of the present invention is not limited to a frozen and dried composition, and may be a solution obtained by re-dissolving the frozen and dried composition. Glucose can be measured by various forms such as glucose assay kit and glucose sensor. The purified modified protein obtained in this way can be stabilized by the following methods.

The modified protein can be further stabilized by containing a calcium salt such as calcium chloride, calcium acetate and calcium citrate, or an amino acid such as glutamic acid, glutamine, aspartic acid and lysine, or an organic acid such as α-ketoglutaric acid, α-ketogluconic acid and malic acid, or serum albumin alone or in combination.

The modified protein can be further stabilized by making (1) one or two or more compounds selected from the group consisting of aspartic acid, glutamic acid, α-ketoglutaric acid, malic acid, α-ketogluconic acid, α-cyclodextrin and salts thereof and (2) albumin coexist in purified modified protein.

In the frozen and dried composition, the amount of PQQGDH to be contained is different depending on the origin of the enzyme, and typically is used in the range of about 5 to 50% (weight ratio) suitably. The enzyme is suitably used in the range of 100 to 2000 U/mg in terms of enzyme activity.

Salts of aspartic acid, glutamic acid, α-ketoglutaric acid, malic acid and α-ketogluconic acid include salts of sodium, potassium, ammonium, calcium and magnesium, but are not especially limited. It is preferable to add the above compounds and the salts thereof and α-cyclodextrin in the range of 1 to 90% (weight ratio). These substances may be used alone or in combination of two or more.

A buffer contained is not especially limited, and includes Tris buffer, phosphate buffer, boric buffer and Good buffer. The pH value of the buffer is adjusted in the range of about 5.0 to 9.0 depending on a purpose for the use. The amount of the buffer to be contained in the frozen and dried composition is not especially limited, and is preferably 0.1% (weight ratio) or more and especially preferably in the range of 0.1 to 30% (weight ratio).

Usable albumin includes bovine serum albumin (BSA) and ovalbumin (OVA). Especially BSA is preferable. The amount of the albumin to be contained is preferably 1 to 80% (weight ratio), and more preferably 5 to 70% (weight ratio).

The other stabilizer and the like may be further added to the composition in the range in which no especially adverse effect is given to the reaction of PQQGDH. A combination method of the stabilizer of the present invention is not especially limited. Examples of the method include the method of combining the stabilizer in the buffer containing PQQGDH, the method of combining PQQGDH in the buffer containing the stabilizer or the method of simultaneously combining PQQGDH and the stabilizer in the buffer.

A stabilization effect is also obtained by adding calcium ion. That is, the modified protein can be stabilized by containing the calcium ion or the calcium salt. As the calcium salt, calcium salts of inorganic acids and organic acids such as calcium chloride or calcium acetate or calcium citrate are exemplified. It is preferable that the amount of the calcium ion to be contained is $1 \times 10^{-4}$ to $1 \times 10^{-2}$ M in the aqueous composition.

The stabilization effect by containing the calcium ion or the calcium salt is further enhanced by containing the amino acid selected from the group consisting of glutamic acid, glutamine and lysine.

The amino acids selected from the group consisting of glutamic acid, glutamine and lysine may be one or two or more. It is preferable that the amount of the contained amino acid selected from the group consisting of glutamic acid, glutamine and lysine is 0.01 to 0.2% by weight in the above aqueous composition.

Serum albumin may be further contained. When serum albumin is added to the above aqueous composition, it is preferable that the amount to be contained is 0.05 to 0.5% by weight.

The common buffer is used as the buffer, and it is preferable to typically make pH of the composition 5 to 10. Specifically, Tris hydrochloride buffer, boric buffer or Good buffer is used, and all buffers which do not form an insoluble salt with calcium can be used.

Other ingredients, e.g., a surfactant, a stabilizer, an excipient and the like may be added to the above aqueous composition as needed.

The present invention is a glucose assay kit comprising the modified pyrroloquinoline quinone dependent glucose dehydrogenase (PQQGDH) having the lower action property on the disaccharide than the wild type PQQGDH, or a glucose sensor comprising the modified PQQGDH, and a glucose measurement method comprising the modified PQQGDH.

In the present invention, glucose can be measured by the following various methods.

Glucose Assay Kit

The present invention is characterized by the glucose assay kit comprising the modified PQQGDH according to the present invention. The glucose assay kit of the present invention contains the modified PQQGDH according to the present invention in the amount enough to assay at least once. Typically, the kit contains the buffer required for the assay, a mediator, glucose standard solutions for making a calibration curve and instructions for the use in addition to the modified PQQGDH of the present invention. The modified PQQGDH according to the present invention can be provided in various forms, e.g., as a frozen and dried reagent or a solution in an appropriate storage solution. Preferably, the modified PQQGDH of the present invention is provided as a holoenzyme, but can be provided as an apoenzyme and converted into the holoenzyme at use.

Glucose Sensor

The present invention is characterized by the glucose sensor comprising the modified PQQGDH according to the present invention. As an electrode, a carbon electrode, a gold electrode or a platinum electrode is used, and the enzyme of the present invention is immobilized on this electrode. As immobilization methods, there are the method of using a crosslinking reagent, the method of including in macromolecular matrix, the method of coating with a dialysis membrane, a optical crosslinking polymer, a conductive polymer, and a redox polymer. Alternatively, the enzyme may be immobilized in the polymer or absorbed/immobilized on the electrode with an electronic mediator typified by ferrocene or derivatives thereof. Or these may be used in combination. Preferably, the modified PQQGDH of the present invention is immobilized on the electrode as the holoenzyme, but can be immobilized in the apoenzyme form and PQQ can be provided as another layer or in another solution. Typically, the modified PQQGDH of the present invention is immobilized on the carbon electrode using glutaraldehyde, and subsequently glutaraldehyde is blocked by treating with a reagent having an amine group.

The glucose concentration can also be measured as follows. The buffer is placed in a thermostatic cell, PQQ, $CaCl_2$ and the mediator are added, and the temperature is kept constant. As the mediator, potassium ferricyanide and phenazine methosulfate can be used. As an action electrode, the electrode on which the modified PQQGDH has been immobilized is used, and a counter electrode (e.g., platinum electrode) and a reference electrode (e.g., Ag/AgCl electrode) are used. A constant voltage is applied to the carbon electrode, after a current becomes a steady state, a sample containing glucose is added and an increase of the current is measured. The glucose concentration in the sample can be calculated in accordance with the calibration curve made by the glucose solutions with standard concentrations.

When pyrroloquinoline quinone dependent glucose dehydrogenase is used for the biosensor, the enzyme is dissolved in blood of the specimen on its strip. The blood has higher viscosity and lower solubility than water and solvents used for other general reagents. Therefore, it is desirable that the amount of the enzyme to be added on the strip is small as the amount of a protein.

According to the present invention, the specific activity of pyrroloquinoline quinone dependent glucose dehydrogenase is more than 1, preferably 1.1 or more, and more preferably 1.5 or more.

When the specific activity is high, a less amount of the protein to be added is needed. Therefore, in the glucose sensor of the present invention, an upper limit of addition amount of the foregoing stabilizer and the like is reduced, and the higher stability is likely assured.

EXAMPLES

The present invention will be described in detail below based on Examples.

Example 1

Construction of Expression Plasmid of Pyrroloquinoline Quinone Dependent Glucose Dehydrogenase Gene An expression plasmid pNPG5 of the wild type PQQ dependent glucose dehydrogenase was obtained by inserting a structural gene encoding PQQ dependent glucose dehydrogenase derived from *Acinetobacter baumannii* NCIMB11517 strain into a multicloning site of a vector pBluescript SK(−). A base sequence thereof and an amino acid sequence of PQQ dependent glucose dehydrogenase deduced from the base sequence are shown in SEQ ID NOS:2 and 1, respectively.

Example 2

Preparation of Mutant PQQ Dependent Glucose Dehydrogenase

A recombinant plasmid (pNPG5M1) encoding the mutant PQQ dependent glucose dehydrogenase in which glutamine at position 76 had been substituted with asparagine in the amino acid sequence described in SEQ ID NO:1 was acquired based on the recombinant plasmid pNPG5 comprising the wild type PQQ dependent glucose dehydrogenase gene, a synthetic oligonucleotide described in SEQ ID NO:3 and a synthetic oligonucleotide complementary thereto using Quick Change™ Site-Directed Mutagenesis Kit (supplied from Stratagene) by performing mutagenesis according to its protocol and further determining the base sequence.

A recombinant plasmid (pNPG5M2) encoding the mutant PQQ dependent glucose dehydrogenase in which glutamine at position 76 had been substituted with glutamic acid in the amino acid sequence described in SEQ ID NO:1 was acquired based on pNPG5, a synthetic oligonucleotide described in SEQ ID NO:4 and a synthetic oligonucleotide complementary thereto by performing the same way as in the above method.

A recombinant plasmid (pNPG5M3) encoding the mutant PQQ dependent glucose dehydrogenase in which glutamine at position 76 had been substituted with threonine in the amino acid sequence described in SEQ ID NO:1 was acquired based on pNPG5, a synthetic oligonucleotide described in SEQ ID NO:5 and a synthetic oligonucleotide complementary thereto by performing the same way as in the above method.

A recombinant plasmid (pNPG5M4) encoding the mutant PQQ dependent glucose dehydrogenase in which glutamine at position 76 had been substituted with methionine in the amino acid sequence described in SEQ ID NO:1 was acquired based on pNPG5, a synthetic oligonucleotide described in SEQ ID NO:6 and a synthetic oligonucleotide complementary thereto by performing the same way as in the above method.

A recombinant plasmid (pNPG5M5) encoding the mutant PQQ dependent glucose dehydrogenase in which glutamine at position 76 had been substituted with glycine in the amino acid sequence described in SEQ ID NO:1 was acquired based on pNPG5, a synthetic oligonucleotide described in SEQ ID NO:7 and a synthetic oligonucleotide complementary thereto by performing the same way as in the above method.

A recombinant plasmid (pNPG5M6) encoding the mutant PQQ dependent glucose dehydrogenase in which glutamine at position 76 had been substituted with lysine in the amino acid sequence described in SEQ ID NO:1 was acquired based on pNPG5, a synthetic oligonucleotide described in SEQ ID NO:8 and a synthetic oligonucleotide complementary thereto by performing the same way as in the above method.

A recombinant plasmid (pNPG5M7) encoding the mutant PQQ dependent glucose dehydrogenase in which glutamine at position 168 had been substituted with isoleucine in the amino acid sequence described in SEQ ID NO:1 was acquired based on pNPG5, a synthetic oligonucleotide described in SEQ ID NO:9 and a synthetic oligonucleotide complementary thereto by performing the same way as in the above method.

A recombinant plasmid (pNPG5M8) encoding the mutant PQQ dependent glucose dehydrogenase in which glutamine at position 168 had been substituted with valine in the amino acid sequence described in SEQ ID NO:1 was acquired based on pNPG5, a synthetic oligonucleotide described in SEQ ID NO:10 and a synthetic oligonucleotide complementary thereto by performing the same way as in the above method.

A recombinant plasmid (pNPG5M9) encoding the mutant PQQ dependent glucose dehydrogenase in which glutamine at position 168 had been substituted with alanine in the amino acid sequence described in SEQ ID NO:1 was acquired based on pNPG5, a synthetic oligonucleotide described in SEQ ID NO:11 and a synthetic oligonucleotide complementary thereto by performing the same way as in the above method.

A recombinant plasmid (pNPG5M10) encoding the mutant PQQ dependent glucose dehydrogenase in which lysine at position 20 had been substituted with glutamic acid in the amino acid sequence described in SEQ ID NO:1 was acquired based on pNPG5, a synthetic oligonucleotide described in SEQ ID NO:22 and a synthetic oligonucleotide complementary thereto by performing the same way as in the above method.

A recombinant plasmid encoding the mutant PQQ dependent glucose dehydrogenase in which lysine at position 89 had been substituted with glutamic acid in the amino acid sequence described in SEQ ID NO:1 was acquired based on pNPG5, a synthetic oligonucleotide described in SEQ ID NO:23 and a synthetic oligonucleotide complementary thereto by performing the same way as in the above method. A recombinant plasmid (pNPG5M11) encoding the mutant PQQ dependent glucose dehydrogenase in which lysine at position 89 had been substituted with glutamic acid and lysine at position 300 had been substituted with arginine in the amino acid sequence described in SEQ ID NO:1 was acquired further based on this plasmid, a synthetic oligonucleotide described in SEQ ID NO:24 and a synthetic oligonucleotide complementary thereto by performing the same way as in the above method.

A recombinant plasmid (pNPG5M12) encoding the mutant PQQ dependent glucose dehydrogenase in which glutamine at position 246 had been substituted with histidine in the amino acid sequence described in SEQ ID NO:1 was acquired based on pNPG5, a synthetic oligonucleotide described in SEQ ID NO:25 and a synthetic oligonucleotide complementary thereto by performing the same way as in the above method.

A recombinant plasmid (pNPG5M13) encoding the mutant PQQ dependent glucose dehydrogenase in which glutamine at position 168 had been substituted with serine and leucine at position 169 had been substituted with serine in the amino acid sequence described in SEQ ID NO:1 was acquired based on pNPG5, a synthetic oligonucleotide described in SEQ ID NO:26 and a synthetic oligonucleotide complementary thereto by performing the same way as in the above method.

A recombinant plasmid (pNPG5M14) encoding the mutant PQQ dependent glucose dehydrogenase in which glutamine at position 168 had been substituted with alanine and leucine at position 169 had been substituted with aspartic acid in the amino acid sequence described in SEQ ID NO:1 was acquired based on pNPG5, a synthetic oligonucleotide described in SEQ ID NO:27 and a synthetic oligonucleotide complementary thereto by performing the same way as in the above method.

A recombinant plasmid (pNPG5M15) encoding the mutant PQQ dependent glucose dehydrogenase in which glutamine at position 168 had been substituted with serine and leucine at position 169 had been substituted with glutamic acid in the amino acid sequence described in SEQ ID NO:1 was acquired based on pNPG5, a synthetic oligonucleotide described in SEQ ID NO:66 and a synthetic oligonucleotide complementary thereto by performing the same way as in the above method.

A recombinant plasmid (pNPG5M16) encoding the mutant PQQ dependent glucose dehydrogenase in which glutamine at position 168 had been substituted with serine and leucine at position 169 had been substituted with proline in the amino acid sequence described in SEQ ID NO:1 was acquired based on pNPG5, a synthetic oligonucleotide described in SEQ ID NO:67 and a synthetic oligonucleotide complementary thereto by performing the same way as in the above method.

A recombinant plasmid (pNPG5M17) encoding the mutant PQQ dependent glucose dehydrogenase in which glutamine at position 168 had been substituted with alanine and leucine at position 169 had been substituted with glycine in the amino acid sequence described in SEQ ID NO:1 was acquired based on pNPG5, a synthetic oligonucleotide described in SEQ ID NO:68 and a synthetic oligonucleotide complementary thereto by performing the same way as in the above method.

*Escherichia coli* competent cells (JM109 supplied from Toyobo) were transformed with each recombinant plasmid of pNPG5, pNPG5M1, pNPG5M2, pNPG5M3, pNPG5M4, pNPG5M5, pNPG5M6, pNPG5M7, pNPG5M8, pNPG5M9, pNPG5M10, pNPG5M11, pNPG5M12, pNPG5M13, pNPG5M14, pNPG5M15, pNPG5M16 and pNPG5M17 to yield the transformants.

Example 3

Construction of Expression Vector Replicable in Bacteria Belonging to Genus *Pseudomonas*

A structural gene portion of the mutant PQQ dependent glucose dehydrogenase was isolated by cleaving 5 µg of recombinant plasmid pNPG5M1 DNA obtained in Example 2 with restriction enzymes BamHI and XhoI (supplied from Toyobo). The isolated DNA and pTM33 (1 µg) cleaved with BamHI and XhoI were reacted with 1 unit of T4 DNA ligase at 16° C. for 16 hours to ligate the DNA. *Escherichia coli* DH5α competent cells were transformed with the ligated DNA. The resulting expression plasmid was designated as pNPG6M1.

For each recombinant plasmid of pNPG5, pNPG5M2, pNPG5M3, pNPG5M4, pNPG5M5, pNPG5M6, pNPG5M7, pNPG5M8, pNPG5M9, pNPG5M10, pNPG5M11, pNPG5M12, pNPG5M13, pNPG5M14, pNPG5M15, pNPG5M16 and pNPG5M17, the expression plasmid was acquired by the same way as in the above method. The resulting expression plasmids were designated as pNPG6, pNPG6M2, pNPG6M3, pNPG6M4, pNPG6M5, pNPG6M6, pNPG6M7, pNPG6M8, pNPG6M9, pNPG6M10, pNPG6M11, pNPG6M12, pNPG6M13, pNPG6M14, pNPG6M15, pNPG6M16 and pNPG6M17.

Example 4

Preparation of Transformant from Bacteria Belonging to Genus *Pseudomonas*

*Pseudomonas putida* TE3493 (Bikokenki No. 12298) was cultured in LBG medium (LB medium+0.3% glycerol) at 30° C. for 16 hours, and microbial cells were collected by centrifugation (12,000 rpm, 10 minutes). Ice-cooled 5 mM K-phosphate buffer (pH 7.0, 8 mL) containing 300 mM sucrose was added to these microbial cells to suspend the microbial cells. The microbial cells were collected again by centrifugation (12,000 rpm, 10 minutes). Ice-cooled 5 mM K-phosphate buffer (pH 7.0, 0.4 mL) containing 300 mM sucrose was added to these microbial cells to suspend the microbial cells. The expression plasmid pNPG6M1 (0.5 µg) obtained in Example 3 was added to the suspension, and transformation was performed by the electroporation method. An objective transformant was obtained from colonies which had grown in the LB agar medium containing 100 µg/mL of streptomycin.

For each expression plasmid of pNPG6, pNPG6M2, pNPG6M3, pNPG6M4, pNPG6M5, pNPG6M6, pNPG6M7, pNPG6M8, pNPG6M9, pNPG6M10, pNPG6M11, pNPG6M12, pNPG6M13, pNPG6M14, pNPG6M15, pNPG6M16 and pNPG6M17, the transformants were acquired by the same way as in the above method.

Test Example 1

Method of Measuring GDH Activity (Used for Measurements Other than Specific Activity Measurement)

Principle of Measurement

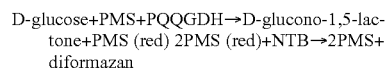

D-glucose+PMS+PQQGDH→D-glucono-1,5-lactone+PMS (red) 2PMS (red)+NTB→2PMS+ diformazan The presence of diformazan formed by reduction of nitrotetrazolium blue (NTB) by phenazine methosulfate (PMS) (red) was measured by spectrophotometry at 570 nm.

Definition of Unit

One unit refers to the amount of the enzyme of PQQGDH to form 0.5 mM of diformazan per one minute under the following condition.

(3) Method

Reagent

A. Glucose solution: 0.5 M (0.9 g D-glucose, molecular weight: 180.16)/10 mL $H_2O$ B. PIPES-NaOH buffer pH 6.5: 50 mM (1.51 g of PIPES [molecular weight: 302.36] was suspended in 60 mL of water) was dissolved in 5 N NaOH, and 2.2 mL of 10% Triton-X100 is added. pH was adjusted to 6.5±0.05 at 25° C. using 5 N NaOH, and water was added to make 100 mL.)
C. PMS solution: 3.0 mM (9.19 mg of phenazine methosulfate [molecular weight: 817.65])/10 mL $H_2O$
D. NTB solution: 6.6 mM (53.96 mg of nitrotetrazolium blue [molecular weight: 817.65])/10 mL $H_2O$
E. Enzyme dilution solution: 50 mM PIPES-NaOH buffer (pH 6.5) containing 1 mM $CaCl_2$, 0.1% Triton X100 and 0.1% BSA Procedure The following reaction mixture was prepared in a light shielding bottle, and stored on ice (prepared at use).
1.8 mL of D-glucose solution (A)
24.6 mL of PIPES-NaOH solution (pH 6.5) (B)
2.0 mL of PMS solution
1.0 mL of NTB solution (D)

TABLE 1

| Concentration in assay mixture | |
| --- | --- |
| PIPES buffer | 42 mM |
| D-glucose | 30 mM |
| PMS | 0.20 mM |
| NTB | 0.22 mM |

The reaction mixture (3.0 mL) was placed in a test tube (made from plastic), which was then preliminarily heated at 37° C. for 5 minutes. The enzyme solution (0.1 mL) was added, and mixed by gently inverting.

The increase of absorbance for water at 570 nm was recorded by a spectrophotometer for 4 to 5 minutes with keeping the temperature at 37° C., and ΔOD per minute was calculated from an initial linear part of a curve (OD test).

At the same time, the same method except for adding the enzyme dilution solution (E) in place of the enzyme solution was repeated to measure a blank (ΔOD blank).

The enzyme powder was dissolved in the ice-cooled enzyme dilution solution (E) just before the assay, and diluted with the same buffer to 0.1 to 0.8 U/mL (due to adhesiveness of the enzyme, it is preferable to use the plastic tube).

The activity is calculated using the following formulae:

$$U/ml = \{\Delta OD/\min(\Delta OD\text{ test} - \Delta OD\text{ blank}) \times Vt \times df\} / (20.1 \times 1.0 \times Vs)$$

$$U/mg = (U/ml) \times 1/C$$

Vt: total volume (3.1 mL)
Vs: sample volume (1.0 mL)
20.1: ½ mM molecular absorbance coefficient of diformazan
1.0: light path length (cm)
df: dilution coefficient
C: enzyme concentration in solution (c mg/mL)

Method of Preparing Holo Type Expression Purified Enzyme (Applied Only to Example 1 to 14)

Terrific broth (500 mL) was placed in a 2 L Sakaguchi flask, autoclaved at 121° C. for 20 minutes, and after cooling, 100 μg/mL of streptomycin separately sterilized was added. A culture solution (5 mL) obtained by previously culturing *Pseudomonas putida* TE3493(pNPG6M1) in PY medium containing 100 μg/mL of streptomycin at 30° C. for 24 hours was inoculated to this medium, and the aeration stirring culture was performed at 30° C. for 40 hours. The PQQ dependent glucose dehydrogenase activity at the termination of the culture was about 120 U per mL of the culture solution in the above activity measurement.

The above microbial cells were collected by the centrifugation, suspended in 20 mM phosphate buffer (pH 7.0), and subsequently disrupted by sonication. Further the centrifugation was performed, and a supernatant solution was obtained as a crude enzyme solution. The resulting crude enzyme solution was separated and purified by HiTrap-SP (Amersham-Pharmacia) ion-exchange column chromatography. Then, the enzyme solution was dialyzed against 10 mM PIPES-NaOH buffer (pH 6.5), and calcium chloride was added at a final concentration of 1 mM. Finally, the separation/purification was performed by HiTrap-DEAE (Amersham-Pharmacia) ion-exchange column chromatography to obtain a purified enzyme preparation. The preparation obtained by the present method exhibited a nearly single band on SDS-PAGE.

Also for *Pseudomonas putida* TE3493 transformants transformed with pNPG6, pNPG6M2, pNPG6M3, pNPG6M4, pNPG6M5, pNPG6M6, pNPG6M7, pNPG6M8, pNPG6M9, pNPG6M10, pNPG6M11, pNPG6M12, pNPG6M13, pNPG6M14, pNPG6M15, pNPG6M16, pNPG6M17, the purified enzyme preparations were acquired by the same way as in the above method.

Performances of the purified enzymes obtained in this way were evaluated.

Measurement of Km Value

In accordance with the above method of measuring the activity, the PQQGDH activity was measured. The Km value for glucose was measured by changing the substrate concentration in the above method of measuring the activity. The Km value for maltose was measured by replacing the glucose solution with a maltose solution in the above method of measuring the activity and changing the substrate concentration as was the case with the measurement of the Km value for glucose. Results are shown in Tables 2A, 2B, 6, 9 and 14.

Substrate Specificity (Applied to Only Examples 1 to 14)

In accordance with the above method of measuring the activity, the PQQGDH activity was measured. The dehydrogenase activity value in the case of using glucose as the substrate and the dehydrogenase activity value in the case of using maltose as the substrate were measured, and when the measured value in the case of using glucose as the substrate was 100, a relative value was calculated. When the activity was measured in the case of using maltose as the substrate, 0.5 M maltose solution was prepared and used for the activity measurement. The results are shown in Tables 2A, 2B, 4, 5, 6, 8, 9, 11, 13 and 14.

Measurement of Thermal Stability

Various PQQGDH were stored in the buffer (10 mM PIPES-NaOH, pH 6.5 containing 1 mM $CaCl_2$ and 1 μM PQQ) at an enzyme concentration of 5 U/mL, and an activity survival rate after heat treatment at 58° C. was obtained. The results are shown in Tables 2A, 2B, 6, 9 and 14. The heat treatment was performed for 30 minutes only in the test in Table 2B, and for 20 minutes in the other tests.

Measurement of Optimal pH

The enzyme activity was measured in 50 mM phosphate buffer (pH 5.0 to 8.0) containing 0.22% Triton-X100, 50 mM acetate buffer (pH 3.0 to 6.0) containing 0.22% Triton-X100, 50 mM PIPES-NaOH buffer (pH 6.0 to 7.0) containing 0.22% Triton-X100 and 50 mM Tris hydrochloride buffer (pH 7.0 to 9.0) containing 0.22% Triton-X100. The results are shown in FIG. 1. The pH values at which the highest activity was exhibited are shown in Table 2A. In the table, the specific activity is represented by the enzyme activity (U/mL)/absorbance at 280 nm (ABS). Km (Mal) and Km (Glc) represent the Km values for maltose and glucose, respectively.

TABLE 2

A

| Mutant | specific activity | Substrate specificity | Km (Mal) | Km (Glc) | Optimal pH | Thermal stability |
|---|---|---|---|---|---|---|
| Q76N | 49 | 66% | 13.6 | 3.1 | 6.4 | 49.1% |
| Q76E | 36 | 68% | 13.6 | 3.7 | 5.6 | 42.5% |
| Q76T | 32 | 84% | 10.3 | 2.5 | 6.4 | 49.0% |
| Q76M | 108 | 81% | 8.7 | 2.2 | 6.4 | 55.3% |
| Q76G | 32 | 84% | 10.6 | 2.2 | 6.4 | 58.5% |
| Q76K | 84 | 32% | 29.9 | 7.9 | 6.8 | 48.4% |
| Q168I | 231 | 69% | 11.9 | 5.3 | 6.8 | 27.3% |
| Q168V | 377 | 71% | 13.0 | 6.4 | 6.4 | 32.2% |
| Q168A | 333 | 37% | 35.3 | 10.4 | 6.4 | 59.2% |
| Wild | 1469 | 103% | 4.1 | 6.5 | 6.4 | 46.7% |

B

| Mutant | Specific activity | Substrate specificity | Thermal stability |
|---|---|---|---|
| K20E | 924 | 105% | 49.7% |
| Q76M | 108 | 81% | 52.3% |
| Q76G | 32 | 84% | 55.1% |
| K89E + K300R | 1038 | 81% | 58.8% |
| Q168A | 333 | 37% | 55.8% |
| Q246H | 686 | 192% | 82.2% |
| Q168S + L169S | 288 | 33% | 73.0% |
| Q168A + L169D | 106 | 18% | 78.8% |
| Q168S + L169E | 270 | 19% | 47.0% |
| Q168S + L169P | 460 | 25% | 47.2% |
| Q168A + L169G | 170 | 18% | 78.3% |
| Wild type | 1469 | 103% | 43.4% |

Note)
Specific activity: enzyme activity (U/mL)/absorbance at 280 nm (ABS)
Km(Mal): Km value for maltose
Km(Glc): Km value for glucose
Note)
Specific activity: enzyme activity (U/mL)/absorbance at 280 nm Confirmation of Quantitative Property of Q76K The following reaction reagent containing 0.45 U/mL of Q76K was prepared
 50 mM PIPES-NaOH buffer (pH 6.5)
 1 mM CaCl$_2$
 0.22% Triton X-100
 0.4 mM PMS
 0.26 mM WST-1 (water-soluble tetrazolium-salt supplied from Dojindo Laboratories)

In accordance with the method of measuring the glucose amount shown below, as samples, purified water, serial dilutions in 10 levels of 100 mg/dL of standard solution and the glucose aqueous solution (600 mg/dL) were measured, and their linearity was confirmed. The results are shown in FIG. 2.

Method of Measuring Glucose Amount

The reagent (300 μL) was added to 3 μL of the sample, the change of absorbance for one minute from two minutes after adding the reagent was obtained, and the glucose amount in the sample was calculated based on a two point working line obtained from the purified water and the standard solution of 100 mg/dL glucose. As a measuring device, Hitachi 7150 type automatic analyzer was used, only a main wavelength of 480 nm was used for the measurement, and the measurement was performed at 37° C.

Figure 2:
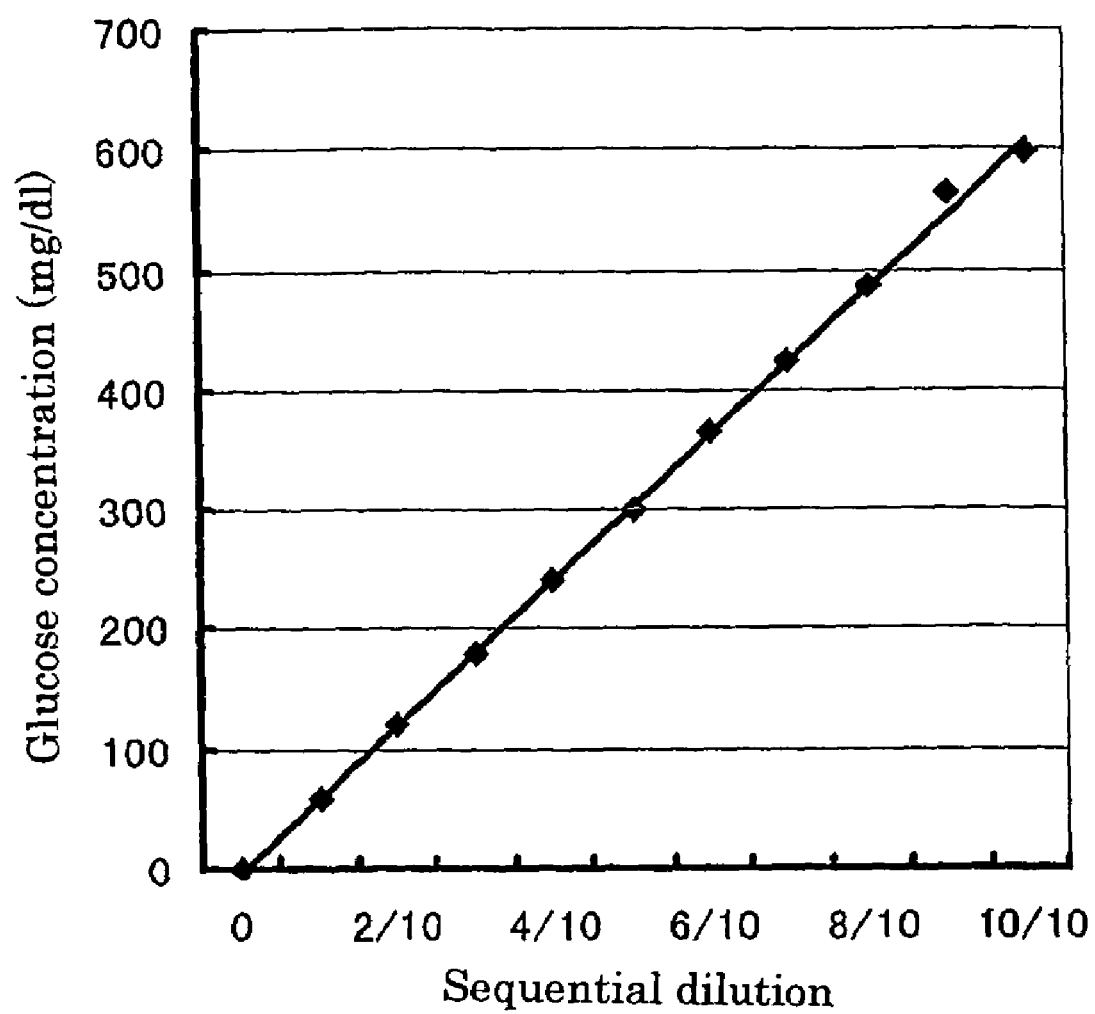
FIG. 2 is a view showing the result of confirming a glucose quantitative property of Q76K. A horizontal axis and a vertical axis represent sequential dilution of one level and a measured value (mg/dl) of a glucose concentration.

By FIG. 2, the good linearity was confirmed in the range of 0 to 600 mg/dL.

Confirmation of Action Property of Q76K on Maltose

The following reaction reagent containing 0.45 U/mL of Q76K was prepared
 50 mM PIPES-NaOH buffer (pH 6.5)
 1 mM CaCl$_2$
 0.22% Triton X-100
 0.4 mM PMS
 0.26 mM WST-1 (supplied from Dojindo Laboratories)

Figure 3:
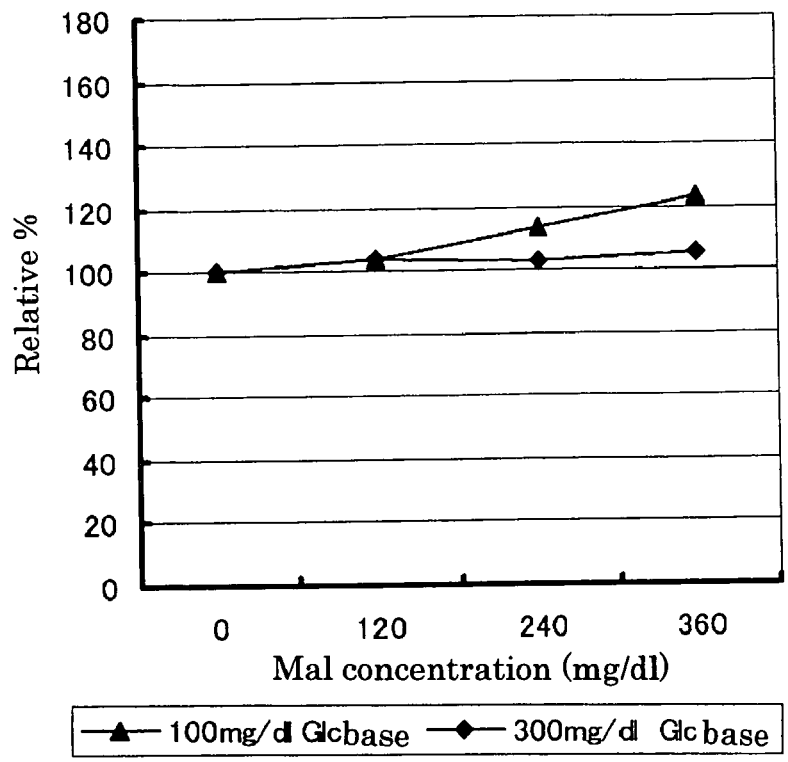
FIG. 3 is a view showing the result of confirming an action property of Q76K on maltose. A horizontal axis represents a concentration (mg/dl) of added maltose, and a vertical axis represents relative % using a measured value when no maltose was added as 100%. In the figure, black triangles represent the cases of using a sample of 100 mg/dl glucose as a base to which maltose was added, and black lozenges represent the cases of using a sample of 300 mg/dl glucose as a base to which maltose was added.

The samples were prepared by adding 0, 120, 240, and 360 mg/dL of maltose to 100 or 300 mg/dL of glucose as the base. In accordance with the above method of measuring the glucose amount, the measurement was performed. The measured value of 100 mg/dL of glucose containing no maltose made 100, and the samples containing 100 mg/dL of glucose as the base were relatively evaluated. Likewise, the measured value of 300 mg/dL of glucose containing no maltose made 100, and the samples containing 300 mg/dL of glucose as the base were relatively evaluated. The results are shown in FIG. 3.

Confirmation of Action Property of Q76E on Maltose

Figure 4:
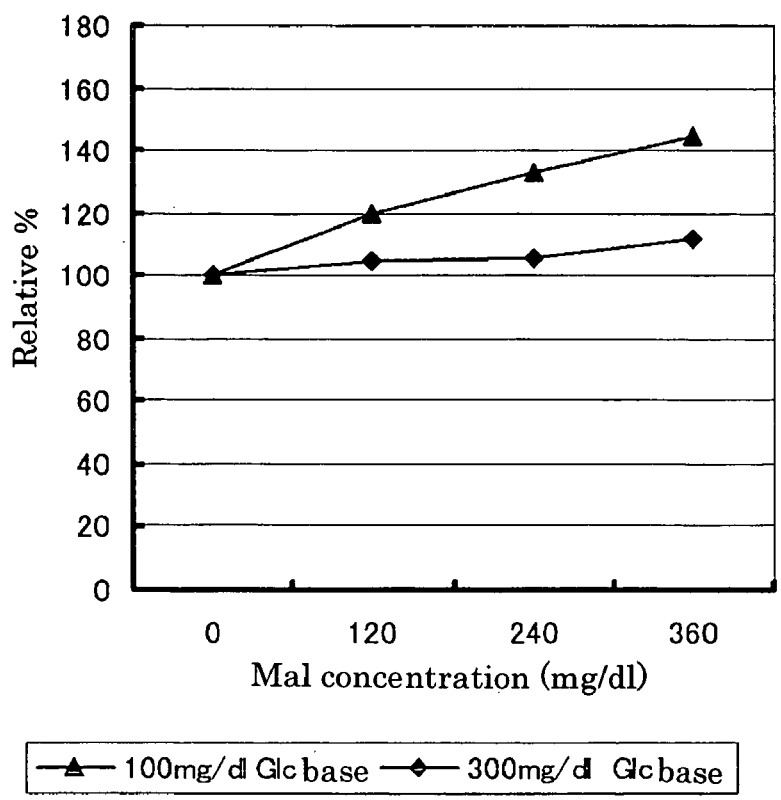
FIG. 4 is a view showing the result of confirming an action property of Q76E on maltose. A horizontal axis represents a concentration (mg/dl) of added maltose, and a vertical axis represents relative % using a measured value when no maltose was added as 100%. In the figure, black triangles represent cases of using a sample of 100 mg/dl glucose as a base to which maltose was added, and black lozenges represent cases of using a sample of 300 mg/dl glucose as a base to which maltose was added.

As was the case with confirmation of the action property of Q76K on maltose, the action property was evaluated using Q76E. The enzyme was added at a concentration of 0.24 U/mL. The results are shown in FIG. 4.

Confirmation of Action Property of Q168V on Maltose

Figure 5:
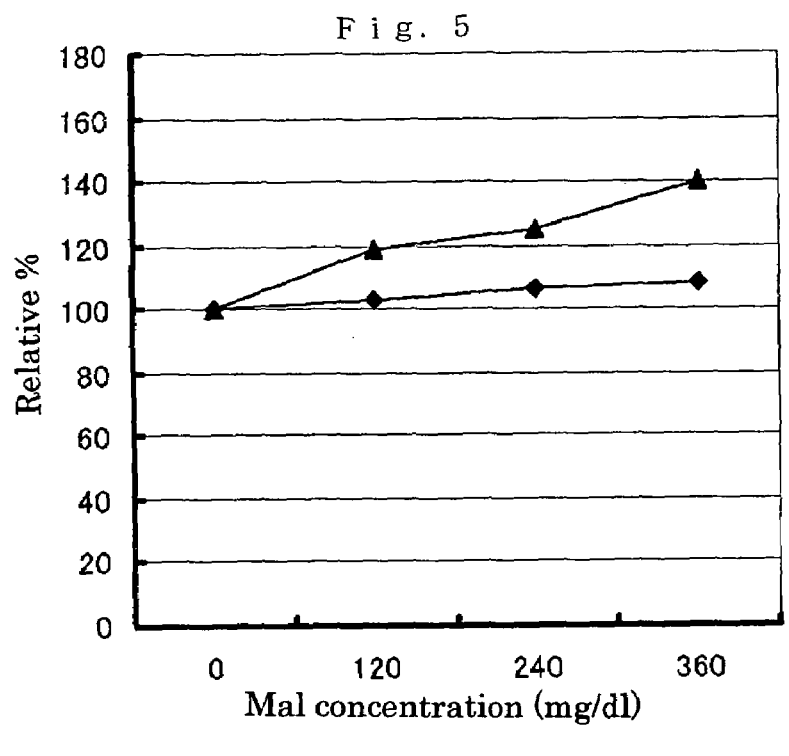
FIG. 5 is a view showing the result of confirming an action property of Q168V on maltose. A horizontal axis represents a concentration (mg/dl) of added maltose, and a vertical axis represents relative % using a measured value when no maltose was added as 100%. In the figure, black triangles represent cases of using a sample of 100 mg/dl glucose as a base to which maltose was added, and black lozenges represent cases of using a sample of 300 mg/dl glucose as a base to which maltose was added.

As was the case with confirmation of the action property of Q76K on maltose, the action property was evaluated using Q168V. The enzyme was added at a concentration of 0.35 U/mL. The results are shown in FIG. 5.

Confirmation of Action Property of Q168A on Maltose

Figure 6:
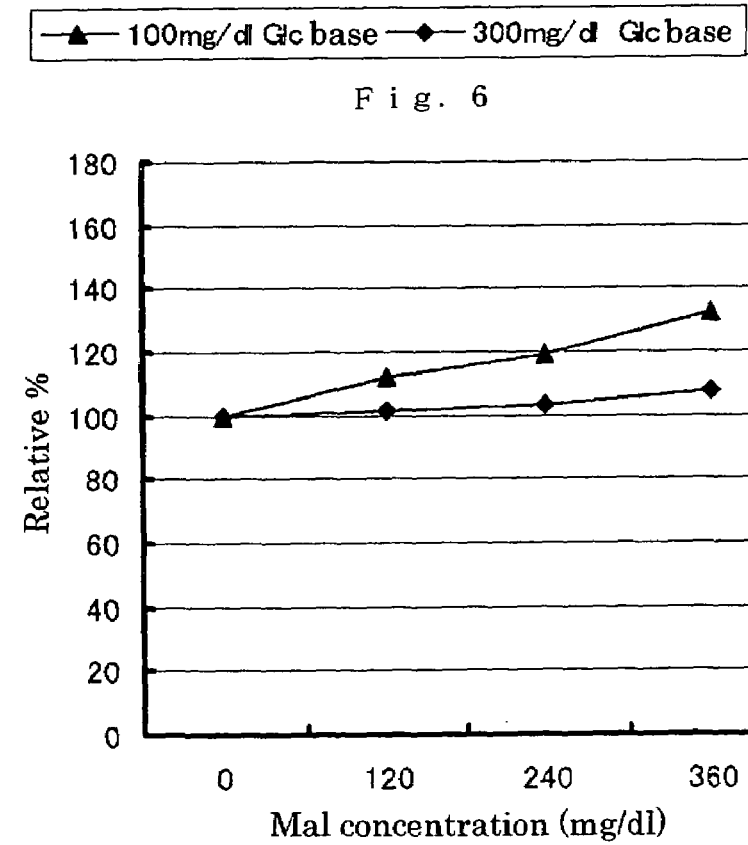
FIG. 6 is a view showing the result of confirming an action property of Q168A on maltose. A horizontal axis represents a concentration (mg/dl) of added maltose, and a vertical axis represents relative % using a measured value when no maltose was added as 100%. In the figure, black triangles represent cases of using a sample of 100 mg/dl glucose as a base to which maltose was added, and black lozenges represent cases of using a sample of 300 mg/dl glucose as a base to which maltose was added.

As was the case with confirmation of the action property of Q76K on maltose, the action property was evaluated using Q168A. The enzyme was added at a concentration of 0.6 U/mL. The results are shown in FIG. 6.

Confirmation of Action Property of Wild Type Enzyme on Maltose

Figure 7:
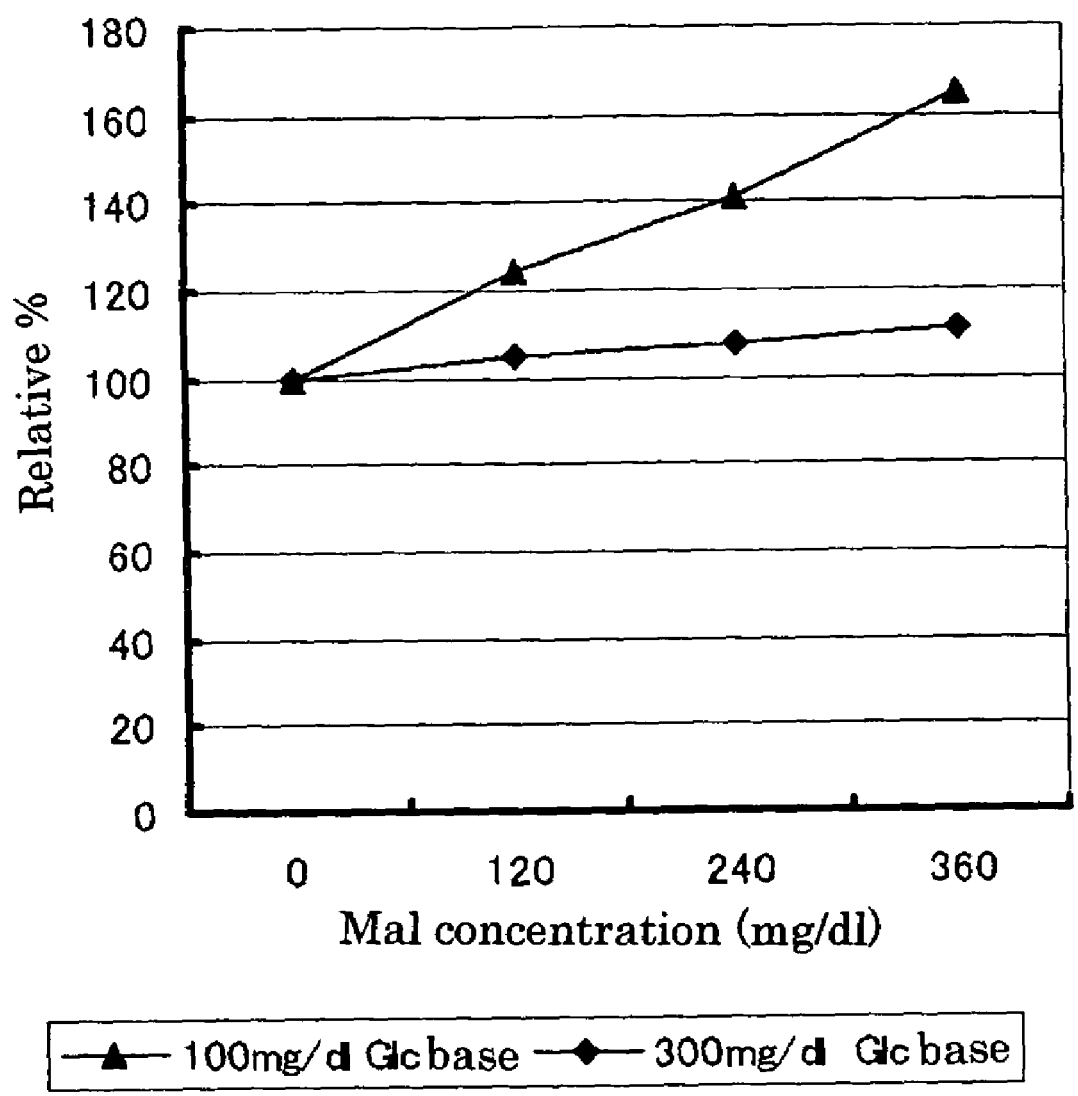
FIG. 7 is a view showing the result of confirming an action property of the wild type on maltose. A horizontal axis represents a concentration (mg/dl) of added maltose, and a vertical axis represents relative % using a measured value when no maltose was added as 100%. In the figure, black triangles represent cases of using a sample of 100 mg/dl glucose as a base to which maltose was added, and black lozenges represent cases of using a sample of 300 mg/dl glucose as a base to which maltose was added.

As was the case with confirmation of the action property of Q76K on maltose, the action property was evaluated using the wild type enzyme. The enzyme was added at a concentration of 0.1 U/mL. The results are shown in FIG. 7.

It was confirmed that the action property on maltose was lowered in Q76K, Q76E, Q168V and Q168A compared with the wild type enzyme from the results in FIGS. 3, 4, 5, 6 and 7.

Example 5

Construction of Mutant Library and Screening

Random mutation was inserted into the region at positions 167 to 169 of the structural gene by PCR with the expression plasmidpNPG5 as a template. The PCR was performed in the solution of the composition shown in Table 3 under the condition at 98° for 2 minutes, then of 30 cycles at 98° for 20 seconds, 60° for 30 seconds and 72° for 4 minutes.

TABLE 3

| Reagent | Amount |
|---|---|
| KOD Dash DNA polymerase (2.5 U/μl) | 1.0 μl |
| Template DNA | 1.0 μl |
| Forward primer (SEQ ID NO: 12) | 2.5 μl |
| Reverse primer (SEQ ID NO: 13) | 2.5 μl |
| 10× buffer | 5.0 μl |
| 2 mM dNTPs | 5.0 μl |
| H$_2$O | 33.0 μl |

*Escherichia coli* DH5α ( strain was transformed with the resulting mutant library, formed each colony was inoculated in a microtiter plate to which 180 μL/well of LB medium (containing 100 μg/mL of ampicillin and 26 μM PQQ) had been dispensed, and cultured at 37° C. for 24 hours. Each culture solution (50 μL) was transferred to another microtiter plate, and cultured microbial cells were disrupted by repeating the freezing and drying. Subsequently, the centrifugation (2000 rpm, 10 minutes) was performed, and the supernatant was collected. The collected supernatant was dispensed by each 10 μL in two microtiter plates. The activity was measured using the activity measuring reagent with glucose as the substrate in one microtiter plate, and the activity was measured using the activity measuring reagent with maltose as the substrate in another microtiter plate. Then the reactivity was compared. Many clones which exhibited the change of reactivity for maltose were obtained.

The clone which exhibited the change of reactivity for maltose was cultured in a test tube to which 5 mL of LB medium (containing 100 μg/mL of ampicillin and 26 μM PQQ) had been dispensed, and confirmation experiments were performed. Consequently, many clones which exhibited the change of reactivity for maltose were obtained.

The results are shown in Table 4.

TABLE 4

| Mutation site | Action property on maltose |
|---|---|
| N167E + Q168G + L169T | 64% |
| Q168G + L169T | 42% |
| N167L + Q168S + L169G | 45% |
| Q168N + L169N + S189R | 51% |
| N167G + Q168R + L169A | 66% |
| N167G + Q168V + L169S | 42% |
| N167T + Q168I + L169S | 42% |
| N167G + Q168S + L169N | 50% |
| Q168R + L169C | 29% |
| Q168C + L169S | 33% |
| N167G + Q168T + L169A + S207C | 24% |
| N167G + Q168S + L169G | 34% |
| N167G + Q168D + L169K | 35% |
| N167G + Q168N + L169S | 59% |
| N188I + T349S | 64% |
| N167G + Q168T + L169G | 28% |
| N167G + Q168V + L169T | 43% |
| Q168R + L169A | 72% |
| N167G + Q168T | 69% |
| Q168I + L169G + K300T | 24% |
| N167T + Q168L + L169K | 63% |
| N167E + Q168S | 32% |
| N167G + Q168G + L169C | 37% |
| Q168A + L169D | 16% |
| Q168S + L169S | 26% |
| N167S + Q168S + L169S | 51% |
| N167A + Q168S + L169S | 40% |
| Q168S + L169P | 20% |
| Q168S + L169E | 15% |
| N167S + Q168N + L169R | 80% |
| N167G + Q168S + L169Y | 55% |
| N167G + Q168S + L169S + L174F + K49N | 39% |
| N167E + Q168G + L169A + S189G | 58% |
| N167S + Q168G + L169A | 48% |
| N167S + Q168V + L169S | 71% |
| N167G + Q168W + L169N | 72% |
| N167G + Q168S + L169V | 36% |
| N167S + Q168L + L169G | 41% |
| N167T + Q168N + L169K | 68% |
| N167A + Q168A + L169P | 63% |
| N167G + Q168G | 46% |
| Q168P + L169G | 23% |
| Q168S + L169G | 22% |
| N167G + Q168G + L169A + F215Y | 32% |
| Q168G + L169V | 43% |
| N167E + Q168N + L169A | 52% |
| N167G + Q168R | 23% |
| N167G + Q168T + L169Q | 72% |
| N167G + Q168A | 33% |
| N167M + Q168Y + L169G | 60% |

TABLE 4-continued

| Mutation site | Action property on maltose |
|---|---|
| N167G + Q168T + L169V + S189G | 42% |
| N167G + Q168K + L169D | 41% |
| Q168S + E245D | 29% |
| A351T | 74% |
| Q168I + L169Q | 51% |
| Q168A | 35% |
| Q168A + L169G | 16% |

Likewise, the mutation was inserted into the region of the positions 67 to 69 (forward primer: SEQ ID NO:14, reverse primer: SEQ ID NO:15), the region of the positions 129 to 131 (forward primer: SEQ ID NO:16, reverse primer: SEQ ID NO:17), and the region of the positions 341 to 343 (forward primer: SEQ ID NO:18, reverse primer: SEQ ID NO:19). The mutation was also attempted to be inserted between the positions 428 to 429 (forward primer: SEQ ID NO:20, reverse primer: SEQ ID NO:21). The results are shown in Table 5.

TABLE 5

| Region of positions 67 to 69 | |
|---|---|
| Mutation site | Action property on maltose |
| P67K + E68K | 79% |
| P67D + E68T + I69C | 60% |
| P67R + E68R + I69C | 80% |

| Region of positions 129 to 131 | |
|---|---|
| Mutation site | Action property on maltose |
| E129R + K130G + P131G | 73% |
| E129N + P131T | 67% |
| E129Q + K130T + P131R | 80% |
| E129A + K130R + P131K | 70% |

| Region of positions 341 to 343 | |
|---|---|
| Mutation site | Action property on maltose |
| E341L + M342P + A343R | 80% |
| A343I | 45% |
| E341P + M342V + A343R | 76% |
| E341S + M342I | 80% |
| E341P + M342V + A343C | 50% |
| E341L + M342R + A343N | 51% |

| Insertion between positions 428 and 429 | |
|---|---|
| Inserted amino acid | Action property on maltose |
| L | 73% |
| K | 79% |
| A | 71% |

Among them, the mutants (Q168S+E245D, Q168A+L169D, Q168S+L169S, Q168S+L169E, Q168A+L169G, Q168S+L169P) in which the action property on maltose has largely lowered were selected, and the plasmids were extracted from these mutants. According to the methods described in Examples 3 and 4, *Pseudomonas* was transformed to express the holoenzyme, and the purified enzymes were acquired and their properties were evaluated. The results are shown in Table 6. In Table 6, the specific activity is represented by the enzyme activity (U/mL)/absorbance at 280 nm

TABLE 6

| Mutation | Specific activity | Substrate specificity | Km(Mal) | Km(Glc) | Thermal stability |
|---|---|---|---|---|---|
| Q168S + E245D | 714 | 29% | 24.3 | 14.4 | 55.5% |
| Q168A + L169D | 106 | 18% | 65.9 | 20.8 | 89.4% |
| Q168S + L169S | 288 | 33% | 55.1 | 14.4 | 83.9% |
| Q168S + L169P | 460 | 25% | 87.1 | 24.1 | 76.3% |
| Q168A + L169G | 170 | 18% | 60.4 | 18.6 | 89.5% |
| Q168S + L169E | 270 | 19% | 70.7 | 8.9 | 63.3% |
| Q168A | 313 | 43% | | | 64.4% |
| Wild type | 1469 | 110% | | | 59.8% |

Note:
specific activity: enzyme activity (U/mL)/absorbance at 280 nm

Example 6

Effect of Mutation at Position Q168 on Substrate Specificity

According to the method described in Example 5, each mutant of Q168C, Q168D, Q168E, Q168F, Q168G, Q168H, Q168K, Q168L, Q168M, Q168N, Q168P, Q168R, Q168S, Q168T, Q168W and Q168Y was prepared. The primers used for the preparation of the mutants are shown in Table 7. The results of comparing the reactivity to maltose using a disruption solution prepared by test tube culture using prepared each mutant are shown in Table 8. Furthermore the plasmid was extracted from each mutant, according to the methods described in Examples 3 and 4, *Pseudomonas* was transformed to express the holoenzyme, and the purified enzymes were acquired and their properties were evaluated. The results are shown in Table 9. In Table 9, the specific activity is represented by the enzyme activity (U/mL)/absorbance at 280 nm

TABLE 7

| Mutation site | Forward primer | Reverse primer |
|---|---|---|
| Q168C | SEQ ID NO: 22 | SEQ ID NO: 23 |
| Q168D | SEQ ID NO: 22 | SEQ ID NO: 24 |
| Q168E | SEQ ID NO: 22 | SEQ ID NO: 25 |
| Q168F | SEQ ID NO: 22 | SEQ ID NO: 26 |
| Q168G | SEQ ID NO: 22 | SEQ ID NO: 27 |
| Q168H | SEQ ID NO: 22 | SEQ ID NO: 28 |
| Q168K | SEQ ID NO: 22 | SEQ ID NO: 29 |
| Q168L | SEQ ID NO: 22 | SEQ ID NO: 30 |
| Q169M | SEQ ID NO: 22 | SEQ ID NO: 31 |
| Q168N | SEQ ID NO: 22 | SEQ ID NO: 32 |
| Q168P | SEQ ID NO: 22 | SEQ ID NO: 33 |
| Q168R | SEQ ID NO: 22 | SEQ ID NO: 34 |
| Q168S | SEQ ID NO: 22 | SEQ ID NO: 35 |
| Q168T | SEQ ID NO: 22 | SEQ ID NO: 36 |
| Q168W | SEQ ID NO: 22 | SEQ ID NO: 37 |
| Q168Y | SEQ ID NO: 22 | SEQ ID NO: 38 |

TABLE 8

| Mutation site | Action property on maltose |
|---|---|
| Q168C | 54% |
| Q168D | 29% |
| Q168E | 36% |
| Q168F | 43% |
| Q168G | 46% |
| Q168H | 55% |
| Q168K | 83% |
| Q168L | 92% |
| Wild type | 104% |

TABLE 8-continued

| Mutation site | Action property on maltose |
|---|---|
| Q169M | 64% |
| Q168N | 82% |
| Q168P | 103% |
| Q168R | 36% |
| Q168S | 60% |
| Q168T | 94% |
| Q168W | 87% |
| Q168Y | 93% |

TABLE 9

| Mutation | Specific activity | Substrate specificity | Km(Mal) | Km(Glc) | Thermal stability |
|---|---|---|---|---|---|
| Q168C | 55 | 58% | 20.4 | 10.7 | 18.2% |
| Q168D | 102 | 46% | 27.4 | — | 61.4% |
| Q168E | 110 | 51% | 4.7 | 8.6 | 75.4% |
| Q168F | 137 | 52% | 36.4 | 10.3 | 55.5% |
| Q168G | 667 | 78% | 11.1 | — | 78.7% |
| Q168H | 486 | 58% | 10.2 | 5.4 | 76.0% |
| Q168K | 5 | 80% | 9.6 | 2.2 | — |
| Q168L | 110 | 96% | 8.6 | 4.3 | 37.1% |
| Q169M | 190 | 68% | 22.7 | 5.3 | 78.4% |
| Q168N | 68 | 93% | 3.6 | 4.1 | — |
| Q168P | 128 | 106% | 3.5 | 5.1 | 82.3% |
| Q168R | 57 | 60% | 18.4 | 3.8 | 32.9% |
| Q168S | 483 | 81% | 12.5 | 3.7 | 80.1% |
| Q168T | 11 | 103% | 15.0 | 6.9 | — |
| Q168W | 287 | 96% | 5.3 | 3.2 | 59.2% |
| Q168Y | 297 | 99% | 12.1 | 6.9 | 100.0% |
| Wild type | 1285 | 106% | 3.8 | 6.3 | 52.2% |

Note:
specific activity: enzyme activity (U/mL)/absorbance at 280 nm

Example 7

Effects of Mutation at Position L169 on Substrate Specificity

According to the method described in Example 2, each mutant of L169A, L169V, L169H, L169Y, L169K, L169D, L169S, L169N, L169G and L169C was prepared. The primers used for the preparation of the mutants are shown in Table 10. The results of comparing the reactivity to maltose using a disruption solution prepared by test tube culture using prepared each mutant are shown in Table 11.

TABLE 10

| Mutation site | Forward primer | Reverse primer |
|---|---|---|
| L169A | SEQ ID NO: 39 | Synthetic oligonucleotide complementary to SEQ ID NO: 39 |
| L169V | SEQ ID NO: 40 | Synthetic oligonucleotide complementary to SEQ ID NO: 40 |
| L169Y | SEQ ID NO: 41 | Synthetic oligonucleotide complementary to SEQ ID NO: 41 |
| L169H | SEQ ID NO: 42 | Synthetic oligonucleotide complementary to SEQ ID NO: 42 |
| L169K | SEQ ID NO: 43 | Synthetic oligonucleotide complementary to SEQ ID NO: 43 |
| L169D | SEQ ID NO: 44 | Synthetic oligonucleotide complementary to SEQ ID NO: 44 |
| L169S | SEQ ID NO: 45 | Synthetic oligonucleotide complementary to SEQ ID NO: 45 |
| L169N | SEQ ID NO: 46 | Synthetic oligonucleotide complementary to SEQ ID NO: 46 |

TABLE 10-continued

| Mutation site | Forward primer | Reverse primer |
|---|---|---|
| L169G | SEQ ID NO: 47 | Synthetic oligonucleotide complementary to SEQ ID NO: 47 |
| L169C | SEQ ID NO: 48 | Synthetic oligonucleotide complementary to SEQ ID NO: 48 |

TABLE 11

| Mutation site | Action property on maltose |
|---|---|
| L169A | 59% |
| L169V | 78% |
| L169Y | 107% |
| L169H | 85% |
| L169K | 60% |
| Wild type | 97% |
| L169D | 38% |
| L169S | 57% |
| L169N | 74% |
| L169G | 48% |
| L169C | 57% |

Example 8

Effects of Combination of Mutation at Position L169 with Q168A Mutant on Substrate Specificity According to the method described in Example 5, each mutant of Q168A+L169A, Q168A+L169C, Q168A+L169E, Q168A+L169F, Q168A+L169H, Q168A+L169I, Q168A+L169K, Q168A+L169M, Q168A+L169N, Q168A+L169P, Q168A+L169Q, Q168A+L169R, Q168A+L169S, Q168A+L169T, Q168A+L169V, Q168A+L169W and Q168A+L169Y was prepared. The primers used for the preparation of the mutants are shown in Table 12. The results of comparing the reactivity to maltose using a disruption solution prepared by test tube culture using prepared each mutant are shown in Table 13. Furthermore the plasmid was extracted from each mutant, according to the methods described in Examples 3 and 4, *Pseudomonas* was transformed to express the holoenzyme, and the purified enzymes were acquired and their properties were evaluated. The results are shown in Table 14. In Table 14, the specific activity is represented by the enzyme activity (U/mL)/absorbance at 280 nm

TABLE 12

| Mutation site | Forward primer | Reverse primer |
|---|---|---|
| Q168A + L169A | SEQ ID NO: 12 | SEQ ID NO: 49 |
| Q168A + L169C | SEQ ID NO: 12 | SEQ ID NO: 50 |
| Q168A + L169E | SEQ ID NO: 12 | SEQ ID NO: 51 |
| Q168A + L169F | SEQ ID NO: 12 | SEQ ID NO: 52 |
| Q168A + L169H | SEQ ID NO: 12 | SEQ ID NO: 53 |
| Q168A + L169I | SEQ ID NO: 12 | SEQ ID NO: 54 |
| Q168A + L169K | SEQ ID NO: 12 | SEQ ID NO: 55 |
| Q168A + L169M | SEQ ID NO: 12 | SEQ ID NO: 56 |
| Q168A + L169N | SEQ ID NO: 12 | SEQ ID NO: 57 |
| Q168A + L169P | SEQ ID NO: 12 | SEQ ID NO: 58 |
| Q168A + L169Q | SEQ ID NO: 12 | SEQ ID NO: 59 |
| Q168A + L169R | SEQ ID NO: 12 | SEQ ID NO: 60 |
| Q168A + L169S | SEQ ID NO: 12 | SEQ ID NO: 61 |
| Q168A + L169T | SEQ ID NO: 12 | SEQ ID NO: 62 |
| Q168A + L169V | SEQ ID NO: 12 | SEQ ID NO: 63 |
| Q168A + L169W | SEQ ID NO: 12 | SEQ ID NO: 64 |
| Q168A + L169Y | SEQ ID NO: 12 | SEQ ID NO: 65 |

TABLE 13

| Mutation site | Action property on maltose |
|---|---|
| Q168A + L169A | 19% |
| Q168A + L169C | 7% |
| Q168A + L169E | 17% |
| Q168A + L169F | 22% |
| Q168A + L169H | 21% |
| Q168A + L169I | 43% |
| Q168A + L169K | 21% |
| Q168A + L169M | 22% |
| Q168A + L169N | 19% |
| Q168A + L169P | 24% |
| Q168A + L169Q | 42% |
| Q168A + L169R | 42% |
| Q168A + L169S | 14% |
| Q168A + L169T | 24% |
| Q168A + L169V | 34% |
| Q168A + L169W | 33% |
| Q168A + L169Y | 37% |
| Wild type | 104% |

TABLE 14

| Mutation | Specific activity | Substrate specificity | Km(Mal) | Km(Glc) | Thermal stability |
|---|---|---|---|---|---|
| Q168A + L169A | 154 | 19% | 126 | 33.0 | 86.2% |
| Q168A + L169C | 63 | 13% | 103 | 35.6 | 100.0% |
| Q168A + L169E | 90 | 19% | 8.6 | 20.4 | 100.0% |
| Q168A + L169F | 138 | 27% | 44.7 | 10.4 | 80.4% |
| Q168A + L169H | 70 | 27% | 99.2 | 15.5 | 100.0% |
| Q168A + L169I | 43 | 53% | 12.5 | 6.0 | 28.7% |
| Q168A + L169K | 129 | 20% | 20.4 | 26.7 | 100.0% |
| Q168A + L169M | 80 | 23% | 52.3 | 15.6 | — |
| Q168A + L169N | 167 | 22% | 59.1 | 34.5 | 83.5% |
| Q168A + L169P | 377 | 24% | 58.0 | 13.9 | 79.9% |
| Q168A + L169Q | 117 | 49% | 156.9 | 5.4 | 100.0% |
| Q168A + L169R | 32 | 45% | 59.0 | 9.6 | 100.0% |
| Q168A + L169S | 42 | 24% | 15.6 | 21.0 | — |
| Q168A + L169T | 98 | 23% | 33.5 | 15.2 | 83.7% |
| Q168A + L169V | 41 | 27% | 49.1 | 24.7 | 40.4% |
| Q168A + L169W | 91 | 38% | 63.3 | 10.8 | 49.4% |
| Q168A + L169Y | 31 | 52% | 13.6 | 11.6 | 74.3% |
| Wild type | 1285 | 106% | 3.8 | 6.3 | 52.2% |

Note:
specific activity: enzyme activity (U/mL)/absorbance at 280 nm

Example 9

Effects of Mutation at Position A170 on Substrate Specificity

According to the method described in Example 2, each mutant of A170C, A170D, A170E, A170F, A170G, A170H, A170K, A170L, A170M, A170N, A170P, A170R, A170S, A170T, A170W, A170Y, A170V, A170I and A170Q was prepared. For the preparation of each mutant, a synthetic oligonucleotide described in SEQ ID NO:69 was used as the forward primer, and a synthetic oligonucleotide complementary to SEQ ID NO:69 was used as the reverse primer. The objective mutant was acquired by screening the prepared mutant library. The results of comparing the reactivity to maltose using the disruption solution prepared by the test tube culture are shown in Table 15.

TABLE 15

| Mutation site | Action property on maltose |
|---|---|
| A170G | 98% |
| A170V | 91% |
| A170L | 86% |
| A170I | 85% |
| A170S | 100% |
| A170T | 92% |
| A170D | 102% |
| A170E | 103% |
| A170N | 100% |
| A170Q | 99% |
| A170K | 87% |
| A170R | 108% |
| A170C | 92% |
| A170M | 90% |
| A170F | 82% |
| A170Y | 88% |
| A170W | 79% |
| A170H | 98% |
| A170P | 28% |
| Wild type | 98% |

Example 10

Effects of Mutation at Position E245 on Substrate Specificity

According to the method described in Example 2, each mutant of E245C, E245D, E245A, E245F, E245G, E245H, E245K, E245L, E245M, E245N, E245P, E245R, E245S, E245T, E245W, E245Y, E245V, E245I and E245Q was prepared. For the preparation of each mutant, a synthetic oligonucleotide described in SEQ ID NO:70 was used as the forward primer, and a synthetic oligonucleotide complementary to SEQ ID NO:70 was used as the reverse primer. The objective mutant was acquired by screening the prepared mutant library. The results of comparing the reactivity to maltose using the disruption solution prepared by the test tube culture are shown in Table 16.

TABLE 16

| Mutation site | Action property on maltose |
|---|---|
| E245A | 99% |
| E245D | 49% |
| E245F | 64% |
| E245H | 54% |
| E245I | 114% |
| E245K | Disappeared |
| E245L | Disappeared |
| E245M | 69% |
| E245N | 59% |
| E245P | Disappeared |
| E245Q | 72% |
| E245S | 98% |
| E245T | 89% |
| E245V | 85% |
| E245W | 92% |
| E245Y | Disappeared |
| E245R | 94% |
| E245G | 92% |
| E245C | 75% |
| Wild type | 99% |

Example 11

Effects of Mutation at Position N249 on Substrate Specificity

According to the method described in Example 2, each mutant of N249C, N249D, N249A, N249F, N249G, N249H, N249K, N249L, N249M, N249E, N249P, N249R, N249S, N249T, N249W, N249V, N249I and N249Q was prepared. For the preparation of each mutant, a synthetic oligonucleotide described in SEQ ID NO:71 was used as the forward primer, and a synthetic oligonucleotide complementary to SEQ ID NO:71 was used as the reverse primer. The objective mutant was acquired by screening the prepared mutant library. The results of comparing the reactivity to maltose using the disruption solution prepared by the test tube culture are shown in Table 17.

TABLE 17

| Mutation site | Action property on maltose |
|---|---|
| N249G | 82% |
| N249A | 77% |
| N249V | 157% |
| N249L | 94% |
| N249I | 137% |
| N249S | Disappeared |
| N249T | Disappeared |
| N249D | Disappeared |
| N249E | 86% |
| N249Q | 79% |
| N249K | 184% |
| N249R | 191% |
| N249C | 107% |
| N249M | 170% |
| N249F | Disappeared |
| N249W | Disappeared |
| N249H | 343% |
| N249P | Disappeared |
| Wild type | 106% |

Example 12

Effects of Combination with E245D Mutant on Substrate Specificity

According to the method described in Example 2, each mutant of (Q168A+L169G+E245D) and (Q168A+L169P+E245D) was prepared. For the preparation of each mutant, a synthetic oligonucleotide described in SEQ ID NO:72 was used as the forward primer, and a synthetic oligonucleotide complementary to SEQ ID NO:72 was used as the reverse primer. As the template DNA, the plasmid of (Q168A+L169G) or (Q168A+L169P) obtained in Example 8 was used. For the prepared mutants, the results of comparing the reactivity to maltose using the disruption solution prepared by the test tube culture are shown in Table 18.

TABLE 18

| Mutation | Specific activity | Substrate specificity | Km (Mal) | Km (Glc) | Thermal stability |
|---|---|---|---|---|---|
| Q168A + L169G + E245D | 138 | 11% | 228.8 | 59.5 | 97.2 |
| Q168A + L169P + E245D | 382 | 15% | 126.8 | 41.6 | 86.2 |
| Wild type | 1285 | 107% | 3.8 | 6.3 | 49.6% |

Example 13

Effects of Mutation at Position T349 on Substrate Specificity

According to the method described in Example 2, each mutant of T349S, T349P and T349Y was prepared. For the preparation of each mutant, a synthetic oligonucleotide described in SEQ ID NO:73 was used as the forward primer, and a synthetic oligonucleotide complementary to SEQ ID NO:73 was used as the reverse primer. The objective mutant was acquired by screening the prepared mutant library. The results of comparing the reactivity to maltose using the disruption solution prepared by the test tube culture are shown in Table 19.

TABLE 19

| Mutation site | Action property on maltose |
|---|---|
| T349S | 49% |
| T349P | 32% |
| T349Y | 90% |

Example 14

Effects of Mutation at Position N429 on Substrate Specificity

According to the method described in Example 2, each mutant of N429F, N429P, N429L and N429Y was prepared. For the preparation of each mutant, a synthetic oligonucleotide described in SEQ ID NO:74 was used as the forward primer, and a synthetic oligonucleotide complementary to SEQ ID NO:74 was used as the reverse primer. The objective mutant was acquired by screening the prepared mutant library. The results of comparing the reactivity to maltose using the disruption solution prepared by the test tube culture are shown in Table 20.

TABLE 20

| Mutation site | Action property on maltose |
|---|---|
| N429F | 69% |
| N429P | 44% |
| N429L | 97% |
| N429Y | 68% |

Example 101

Construction of Expression Plasmid for PQQ Dependent Glucose Dehydrogenase Gene The same as the method described in Example 1.

Example 102

Preparation of Mutant PQQ Dependent Glucose Dehydrogenase

A recombinant plasmid (pNPG5-74V) encoding the mutant PQQ dependent glucose dehydrogenase in which aspartic acid at position 74 had been substituted with valine in the amino acid sequence described in SEQ ID NO:1 was acquired based on the recombinant plasmid pNPG5 comprising the wild type PQQ dependent glucose dehydrogenase gene, a synthetic oligonucleotide described in SEQ ID NO:75 and a synthetic oligonucleotide complementary thereto using Quick Change™ Site-Directed Mutagenesis Kit (supplied from Stratagene) by performing mutagenesis according to its protocol and further determining the base sequence.

A recombinant plasmid (pNPG5-342I) encoding the mutant PQQ dependent glucose dehydrogenase in which methionine at position 342 had been substituted with isoleucine in the amino acid sequence described in SEQ ID NO:1 was acquired based on pNPG5, a synthetic oligonucleotide described in SEQ ID NO:76 and a synthetic oligonucleotide complementary thereto by performing the same way as in the above method.

Additionally, similarly to the above, using the synthetic oligonucleotide designed to substitute the objective amino acid and the synthetic oligonucleotide complementary thereto, a recombinant plasmid (pNPG5-342V) encoding the mutant PQQ dependent glucose dehydrogenase in which methionine at position 342 had been substituted with valine in the amino acid sequence described in SEQ ID NO:1, a recombinant plasmid (pNPG5-342P) encoding the mutant PQQ dependent glucose dehydrogenase in which methionine at position 342 had been substituted with proline, and a recombinant plasmid (pNPG5-342A) encoding the mutant PQQ dependent glucose dehydrogenase in which methionine at position 342 had been substituted with alanine were obtained. Also, a recombinant plasmid (pNPG5-146A) encoding the mutant PQQ dependent glucose dehydrogenase in which serine at position 146 had been substituted with alanine, a recombinant plasmid (pNPG5-170L) encoding the mutant PQQ dependent glucose dehydrogenase in which alanine at position 170 had been substituted with leucine, a recombinant plasmid (pNPG5-170M) encoding the mutant PQQ dependent glucose dehydrogenase in which alanine at position 170 had been substituted with methionine, a recombinant plasmid (pNPG5-170I) encoding the mutant PQQ dependent glucose dehydrogenase in which alanine at position 170 had been substituted with isoleucine and a recombinant plasmid (pNPG5-170F) encoding the mutant PQQ dependent glucose dehydrogenase in which alanine at position 170 had been substituted with phenylalanine were obtained. The synthetic oligonucleotides are described in SEQ ID NOS:77 to 84.

Escherichia coli competent cells (JM109 supplied from Toyobo) were transformed with respective recombinant plasmids of pNPG5, pNPG5-74V, pNPG5-342I, pNPG5-342V, pNPG5-342P, pNPG5-342A, pNPG5-146A, pNPG5-170L, pNPG5-170M, pNPG5-170I and pNPG5-170F, and the transformants were obtained.

Example 103

Construction of Expression Vector Replicable in Bacteria Belonging to Genus *Pseudomonas*

The structural gene portion of the mutant PQQ dependent glucose dehydrogenase was isolated by cleaving 5 μg of recombinant plasmid pNPG5-74V DNA obtained in Example 102 with restriction enzymes BamHI and XhoI (supplied from Toyobo). The isolated DNA and pTM33 (1 μg) cleaved with BamHI and XhoI were reacted with 1 unit of T4 DNA ligase at 16° C. for 16 hours to ligate the DNA. *Escherichia coli* DH5α competent cells were transformed with the ligated DNA. The resulting expression plasmid was designated as pNPG6-74V.

For each recombinant plasmid of pNPG5, pNPG5-342I, pNPG5-342V, pNPG5-342P, pNPG5-342A, pNPG5-146A, pNPG5-170L, pNPG5-170M, pNPG5-170I and pNPG5-

170F, the expression plasmid was obtained by the same way as in the above method. The resulting expression plasmids were designated as pNPG6, pNPG6-342I, pNPG6-342V, pNPG6-342P, pNPG6-342A, pNPG6-146A, pNPG6-170L, pNPG6-170M, pNPG6-170I and pNPG6-170F.

Example 104

Preparation of Transformant from Bacteria Belonging to Genus *Pseudomonas*

*Pseudomonas putida* TE3493 (Bikokenki No. 12298) was cultured in LBG medium (LB medium+0.3% glycerol) at 30° C. for 16 hours, and microbial cells were collected by centrifugation (12,000 rpm, 10 minutes). Ice-cooled 5 mM K-phosphate buffer (pH 7.0, 8 mL) containing 300 mM sucrose was added to these microbial cells to suspend the microbial cells. The microbial cells were collected again by centrifugation (12,000 rpm, 10 minutes). Ice-cooled 5 mM K-phosphate buffer (pH 7.0, 0.4 mL) containing 300 mM sucrose was added to these microbial cells to suspend the microbial cells.

The expression plasmid pNPG6-74V (0.5 μg) obtained in Example 103 was added to the suspension, and transformation was performed by the electroporation method. An objective transformant was obtained from colonies which had grown in the LB agar medium containing 100 μg/mL of streptomycin.

For each expression plasmid of pNPG6, pNPG6-342I, pNPG6-342V, pNPG6-342P, pNPG6-342A, pNPG6-146A, pNPG6-170L, pNPG6-170M, pNPG6-170I and pNPG6-170F, the transformants were obtained by the same way as in the above method.

Example 105

Preparation of Holo Type Expression Purified Enzyme (Applied Only to Examples 101 to 106)

Terrific broth (500 mL) was placed in a 2 L Sakaguchi flask, autoclaved at 121° C. for 20 minutes, and after cooling, 100 μg/mL of streptomycin separately sterilized was added. A culture solution (5 mL) obtained by previously culturing *Pseudomonas putida* TE3493(pNPG6-74V) in PY medium containing 100 μg/mL of streptomycin at 30° C. for 24 hours was inoculated to this medium, and the aeration stirring culture was performed at 30° C. for 40 hours. The PQQ dependent glucose dehydrogenase activity at the termination of the culture was about 30 U per mL of the culture solution in the above activity measurement.

The above microbial cells were collected by the centrifugation, suspended in 20 mM phosphate buffer (pH 7.0), and subsequently disrupted by sonication. Further the centrifugation was performed, and a supernatant solution was obtained as a crude enzyme solution. The resulting crude enzyme solution was separated and purified by HiTrap-SP (Amersham-Pharmacia) ion-exchange column chromatography. Then, the enzyme solution was dialyzed against 10 mM PIPES-NaOH buffer (pH 6.5), and then calcium chloride was added at a final concentration of 1 mM. Finally, the separation/purification was performed by HiTrap-DEAE (Amersham-Pharmacia) ion-exchange column chromatography to obtain a purified enzyme preparation. The preparation obtained by the present method exhibited a nearly single band on SDS-PAGE.

For *Pseudomonas putida* TE3493 transformants with pNPG6, pNPG6-342I, pNPG6-342V, pNPG6-342P, pNPG6-342A, pNPG6-146A, pNPG6-170L, pNPG6-170M, pNPG6-170I and pNPG6-170F, the purified enzyme preparations were also obtained by the same way as in the above method.

The performances of the purified enzymes obtained in this way were evaluated.

Substrate Specificity (Applied Only to Examples 101 to 106)

According to the above method of measuring the activity, the PQQGDH activity was measured. The dehydrogenase activity value in the case of using glucose as the substrate and the dehydrogenase activity value in the case of using maltose as the substrate were measured, and when the measured value in the case of using glucose as the substrate was 100, the relative value was calculated. When the dehydrogenase activity value in the case of using maltose as the substrate was measured, 0.5 M maltose solution was prepared and used for the activity measurement. The results are shown in Table 102.

In the wild type PQQGDH, the reactivity to glucose and the reactivity to maltose are nearly equal whereas in the modified PQQGDH of the present invention, the reactivity to maltose is lowered.

TABLE 102

| Substituted position of amino acid | Action property on maltose |
| --- | --- |
| M342I | 79 |
| M342V | 74 |
| M342P | 80 |
| M342A | 83 |
| D74V | 90 |
| S146A | 90 |
| A170L | 77 |
| A170M | 76 |
| A170I | 74 |
| A170F | 65 |
| Wild type | 100 |

Example 106

Preparation of Multimutants and Substrate Specificity

Using each plasmid of pNPG5, pNPG5-74V, pNPG5-342I, pNPG5-342V, pNPG5-342P, pNPG5-342A, pNPG5-146A, pNPG5-170L, pNPG5-170M, pNPG5-170I and pNPG5-170F as the template, and using the synthetic oligonucleotide described in SEQ ID NO:80 and the synthetic oligonucleotide complementary thereto, the synthetic oligonucleotide described in SEQ ID NO:85 and designed to substitute glutamine at position 168 with alanine and substitute alanine at position 170 with leucine and the synthetic oligonucleotide complementary thereto, the synthetic oligonucleotide described in SEQ ID NO:86 and designed to substitute glutamine at position 168 with alanine, substitute leucine at position 169 with proline and substitute alanine at position 170 with methionine and the synthetic oligonucleotide complementary thereto, and synthetic oligonucleotide described in SEQ ID NO:87 and designed to substitute glutamic acid at position 245 with aspartic acid and the synthetic oligonucleotide complementary thereto, according to the method described in Example 102, a recombinant plasmid encoding the modified PQQGDH in which serine at position 146 had been substituted with alanine and alanine at position 170 had been substituted with leucine (pNPG5-146A+170L), in the same definition hereinafter, pNPG5-168A+169P+170L, pNPG5-146A+170M, pNPG5-168A+169P+170M, pNPG5-146A+168A+169P+170L, pNPG5-146A+168A+169P+170M, pNPG5-Q168A+L169P+A170L+E245D, pNPG5-168A+169P+170M+245D, pNPG5-146A+342I, pNPG5-168A+169P+170L+342I, pNPG5-168A+169P+170M +342I, pNPG5-146A+342V, pNPG5-168A+169P+170L+342V, pNPG5-168A+169P+170M+342V, pNPG5-146A+342P, pNPG5-168A+169P+170L+342P, pNPG5-168A+169P+170M+342P, pNPG5-146A+342A, pNPG5-168A+169P+170M+342A, pNPG5-168A+169P+170L+342A, pNPG5-168A+169P+170M+342A, pNPG5-74V+146A, pNPG5-74V+168A+169P+170L, pNPG5-74V+168A+169P+170M, pNPG5-168A+169P+170L+245D+342I, pNPG5-168A+169P+170M+245D+342I, pNG5-168A+169P+170L+245D+342V, pNPG5-168A+169P+170M+245D+342V, pNPG5-168A+169P+170L+245D+342A and pNPG5-168A+169P+170M+245D+342A were obtained, and further the transformants thereof were obtained. When the mutations could not be introduced in one mutation introduction, using the different synthetic oligonucleotides, the mutant plasmid was obtained by repeating the same method twice.

Furthermore, according to the methods described in Examples 103 to 105, the purified enzyme preparations of (S146A+A170L), (Q168A+L169P+A170L), (S146A+A170M), (Q168A+L169P+A170M), (S146A+Q168A+L169P+A170L), (S146A+Q168A+L169P+A170M), (Q168A+L169P+A170L+E245D), (Q168A+L169P+A170M+E245D), (S146A+M342I), (Q168A+L169P+A170L+M342I), (Q168A+L169P+A170M+M342I), (S146A+M342V), (Q168A+L169P+A170L+M342V), (Q168A+L169P+A170M+M342V), (S146A+M342P), (Q168A+L169P+A170L+M342P), (Q168A+L169P+A170M+M342P), (S146A+M342A), (Q168A+L169P+A170L+M342A), (Q168A+L169P+A170M+M342A), (D74V+S146A), (D74V+Q168A+L169P+A170L), (D74V+Q168A+L169P+A170M), (Q168A+L169P+A170L+E245D+M342I), (Q168A+L169P+A170M+E245D+M342I), (Q168A+L169P+A170L+E245D+M342V), (Q168A+L169P+A170M+E245D+M342V), (Q168A+L169P+A170L+E245D+M342A) and (Q168A+L169P+A170M+E245D+M342A) were obtained from the respective transformants, and the substrate specificity thereof was evaluated. The results are shown in Table 103.

TABLE 103

| Substituted position of amino acid | Action property on maltose |
|---|---|
| S146A + A170L | 73 |
| Q168A + L169P + A170L | 22 |
| S146A + A170M | 73 |
| Q168A + L169P + A170M | 25 |
| S146A + Q168A + L169P + A170L | 18 |
| S146A + Q168A + L169P + A170M | 22 |
| Q168A + L169P + A170L + E245D | 14 |
| Q168A + L169P + A170M + E245D | 14 |
| S146A + M342I | 75 |
| Q168A + L169P + A170L + M342I | 14 |
| Q168A + L169P + A170M + M342I | 15 |
| S146A + M342V | 73 |
| Q168A + L169P + A170L + M342V | 14 |
| Q168A + L169P + A170M + M342V | 16 |
| S146A + M342P | 76 |
| Q168A + L169P + A170L + M342P | 25 |
| Q168A + L169P + A170M + M342P | 25 |
| S146A + M342A | 78 |
| Q168A + L169P + A170L + M342A | 20 |
| Q168A + L169P + A170M + M342A | 20 |
| D74V + S146A | 78 |
| D74V + Q168A + L169P + A170L | 21 |
| D74V + Q168A + L169P + A170M | 24 |
| Q168A + L169P + A170L + E245D + M342I | 6.9 |
| Q168A + L169P + A170M + E245D + M342I | 8.8 |
| Q168A + L169P + A170L + E245D + M342V | 7.9 |

TABLE 103-continued

| Substituted position of amino acid | Action property on maltose |
|---|---|
| Q168A + L169P + A170M + E245D + M342V | 8.4 |
| Q168A + L169P + A170L + E245D + M342A | 10 |
| Q168A + L169P + A170M + E245D + M342A | 14 |
| Wildtype | 102 |

Example 201

The present invention will be specifically described using each modified pyrroloquinoline quinone dependent glucose dehydrogenase of Q168A, (Q168A+L169G), (Q168A+L169C), (Q168A+L169P), (Q168S+L169E) and (Q168S+L169P) in pyrroloquinoline quinone dependent glucose dehydrogenase described in SEQ ID NO:1. Needless to say, the present invention is not limited to the following Example.

The purified enzyme preparations of the modified pyrroloquinoline quinone dependent glucose dehydrogenase of Q168A, (Q168A+L169G), (Q168A+L169C), (Q168A+L169P), (Q168S+L169E) and (Q168S+L169P) used in this Example were obtained by the following procedure.

Construction of Expression Plasmid of Wild Type PQQ Dependent Glucose Dehydrogenase Gene The expression plasmid pNPG5 of the wild type PQQ dependent glucose dehydrogenase was obtained by inserting the structural gene encoding PQQ dependent glucose dehydrogenase derived from *Acinetobacter baumannii* NCIMB11517 strain into the multicloning site of the vector pBluescript SK(–). The base sequence is shown in SEQ ID NO:2, and the amino acid sequence of QQ dependent glucose dehydrogenase deduced from the base sequence is shown in SEQ ID NO:1.

Preparation of Mutant QQ Dependent Glucose Dehydrogenase

A recombinant plasmid (pNPG5M168A) encoding the mutant PQQ dependent glucose dehydrogenase in which glutamine at position 168 had been substituted with alanine in the amino acid sequence described in SEQ ID NO:1 was acquired based on the recombinant plasmid pNPG5 comprising the wild type PQQ dependent glucose dehydrogenase gene, a synthetic oligonucleotide described in SEQ ID NO:88 and a synthetic oligonucleotide complementary thereto using Quick Change™ Site-Directed Mutagenesis Kit (supplied from Stratagene) by performing mutagenesis according to its protocol and further determining the base sequence.

A recombinant plasmid (pNPG5M168A+169G) encoding the mutant PQQ dependent glucose dehydrogenase in which glutamine at position 168 had been substituted with alanine and leucine at position 169 had been substituted with glycine in the amino acid sequence described in SEQ ID NO:1 was acquired based on pNPG5, a synthetic oligonucleotide described in SEQ ID NO:89 and a synthetic oligonucleotide complementary thereto by performing the same way as in the above method.

A recombinant plasmid (pNPG5M168A+169C) encoding the mutant PQQ dependent glucose dehydrogenase in which glutamine at position 168 had been substituted with alanine and leucine at position 169 had been substituted with cysteine in the amino acid sequence described in SEQ ID NO:1 was acquired based on pNPG5, a synthetic oligonucleotide described in SEQ ID NO:90 and a synthetic oligonucleotide complementary thereto by performing the same way as in the above method.

A recombinant plasmid (pNPG5M168A+169P) encoding the mutant PQQ dependent glucose dehydrogenase in which glutamine at position 168 had been substituted with alanine and leucine at position 169 had been substituted with proline in the amino acid sequence described in SEQ ID NO:1 was acquired based on pNPG5, a synthetic oligonucleotide described in SEQ ID NO:91 and a synthetic oligonucleotide complementary thereto by performing the same way as in the above method.

A recombinant plasmid (pNPG5M168S+169E) encoding the mutant PQQ dependent glucose dehydrogenase in which glutamine at position 168 had been substituted with serine and leucine at position 169 had been substituted with glutamic acid in the amino acid sequence described in SEQ ID NO:1 was acquired based on pNPG5, a synthetic oligonucleotide described in SEQ ID NO:92 and a synthetic oligonucleotide complementary thereto by performing the same way as in the above method.

A recombinant plasmid (pNPG5M168S+169P) encoding the mutant PQQ dependent glucose dehydrogenase in which glutamine at position 168 had been substituted with serine and leucine at position 169 had been substituted with proline in the amino acid sequence described in SEQ ID NO:1 was acquired based on pNPG5, a synthetic oligonucleotide described in SEQ ID NO:93 and a synthetic oligonucleotide complementary thereto by performing the same way as in the above method.

*Escherichia coli* competent cells (JM109 supplied from Toyobo) were transformed with respective recombinant plasmids of pNPG5M168A, pNPG5M168A+169G, pNPG5M168A+169C, pNPG5M168A+169P, pNPG5M168S+169E and pNPG5M168S+169P to yield the respective transformants.

Construction of Expression Vector Replicable in Bacteria Belonging to Genus *Pseudomonas*

The structural gene portion of the mutant PQQ dependent glucose dehydrogenase was isolated by cleaving 5 µg of recombinant plasmid pNPG5M168A DNA with restriction enzymes BamHI and XhoI (supplied from Toyobo). The isolated DNA and pTM33 (1 µg) cleaved with BamHI and XhoI were reacted with 1 unit of T4 DNA ligase at 16° C. for 16 hours to ligate the DNA. *Escherichia coli* DH5α competent cells were transformed with the ligated DNA. The resulting expression plasmid was designated as pNPG6M168A.

Also for each recombinant plasmid of pNPG5M168A+169G, pNPG5M168A+169C, pNPG5M168A+169P, pNPG5M168S+169E and pNPG5M168S+169P, the expression plasmid was obtained by the same way as in the above method. The resulting expression plasmids were designated as pNPG6M168A+169G, pNPG6M168A+169C, pNPG6M168A+169P, pNPG6M168S+169E and pNPG6M168S+169P.

Preparation of Transformant from Bacteria Belonging to Genus *Pseudomonas*

*Pseudomonas putida* TE3493 (Bikokenki No. 12298) was cultured in LBG medium (LB medium+0.3% glycerol) at 30° C. for 16 hours, and microbial cells were collected by centrifugation (12,000 rpm, 10 minutes). Ice-cooled 5 mM K-phosphate buffer (pH 7.0, 8 mL) containing 300 mM sucrose was added to these microbial cells to suspend the microbial cells. The microbial cells were collected again by centrifugation (12,000 rpm, 10 minutes). Ice-cooled 5 mM K-phosphate buffer (pH 7.0, 0.4 mL) containing 300 mM sucrose was added to these microbial cells to suspend the microbial cells.

The expression plasmid pNPG6M168A (0.5 µg) was added to the suspension, and transformation was performed by the electroporation method. An objective transformant was obtained from colonies which had grown in the LB agar medium containing 100 µg/mL of streptomycin.

For pNPG6M168A+169G, pNPG6M168A+169C, pNPG6M168A+169P, pNPG6M168S+169E and pNPG6M168S+169P, the objective transformants were obtained by the same way as in the above method.

Preparation of Holo Type Expression Purified Enzyme

Terrific broth (500 mL) was placed in a 2 L Sakaguchi flask, autoclaved at 121° C. for 20 minutes, and after cooling, 100 µg/mL of streptomycin separately sterilized was added. A culture solution (5 mL) obtained by previously culturing *Pseudomonas putida* TE3493(pNPG6M168A) in PY medium containing 100 µg/mL of streptomycin at 30° C. for 24 hours was inoculated to this medium, and the aeration stirring culture was performed at 30° C. for 40 hours. The microbial cells were collected by the centrifugation, suspended in 20 mM phosphate buffer (pH 7.0), and subsequently disrupted by sonication. Further the centrifugation was performed, and a supernatant solution was obtained as a crude enzyme solution. The resulting crude enzyme solution was separated and purified by HiTrap-SP (Amersham-Pharmacia) ion-exchange column chromatography. Then, the enzyme solution was dialyzed against 10 mM PIPES-NaOH buffer (pH 6.5), and calcium chloride was added at a final concentration of 1 mM. Finally, the separation/purification was performed by HiTrap-DEAE (Amersham-Pharmacia) ion-exchange column chromatography to obtain a purified enzyme preparation. The preparation obtained by the present method exhibited a nearly single band on SDS-PAGE.

For *Pseudomonas putida* TE3493 transformants transformed with pNPG6M168A+169G, pNPG6M168A+169C, pNPG6M168A+169P, pNPG6M168S+169E and pNPG6M168S+169P, the purified enzyme preparations were obtained by the same way as in the above method.

The performances were evaluated using the purified enzymes obtained in this way.

Method of Measuring Pyrroloquinoline Quinone Dependent Glucose Dehydrogenase Activity Using Ferricyanide Ion as Mediator Principle of Measurement

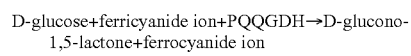

The presence of the ferrocyanide ion produced by reduction of the ferricyanide ion was confirmed by measuring the decrease of absorbance at a wavelength of 420 nm by spectrophotometry.

Definition of Unit

One unit refers to the amount of the enzyme of pyrroloquinoline quinone dependent glucose dehydrogenase to oxidize 1 mM of D-glucose per minute under the following condition.

(3) Method

Reagent

A. Glucose solution: 1 M (1.8 g D-glucose, molecular weight: 180.16)/10 mL $H_2O$ B. PIPES-NaOH buffer pH 6.5: 50 mM (1.51 g of PIPES [molecular weight: 302.36] was suspended in 60 mL of water) was dissolved in 5 N NaOH, and 2.2 mL of 10%

Triton-X100 is added. pH was adjusted to 6.5±0.05 at 25° C. using 5 N NaOH, and water was added to make 100 mL.)
C. Potassium ferricyanide solution: 50 mM (0.165 g of potassium ferricyanide (molecular weight: 329.25)/10 mL $H_2O$
D. Distilled water
E. Enzyme dilution solution: 50 mM PIPES-NaOH buffer (pH 6.5) containing 1 mM $CaCl_2$, 0.1% Triton X100 and 0.1% BSA Procedure
1. The following reaction mixture was prepared in a light shielding bottle, and stored on ice (prepared at use).
   0.9 mL of D-glucose solution (A)
   25.5 mL of PIPES-NaOH solution (pH 6.5) (B)
   2.0 mL of potassium ferricyanide solution (C)
   1.0 mL of distilled water (D)

The concentrations in the reaction mixture are shown in Table 201

TABLE 201

| concentration in reaction mixture | |
|---|---|
| PIPES buffer | 42 mM |
| D-glucose | 30 mM |
| Potassium ferricyanide | 3.4 mM |

2. The reaction mixture (3.0 mL) was placed in a test tube (made from plastic), and preliminarily heated at 37° C. for 5 minutes.
3. The enzyme solution (0.1 mL) was added and gently mixed.
4. The decrease of absorbance for water at 420 nm was recorded by a spectrophotometer for 4 to 5 minutes with keeping the temperature at 37° C., and ΔOD per minute was calculated from an initial linear part of a curve (OD test).

At the same time, the same method except for adding the enzyme dilution solution (E) in place of the enzyme solution was repeated to measure a blank (ΔOD blank).

The enzyme solution was diluted with the ice cooled enzyme dilution solution (E) just before the assay to about 1.0 U/mL (due to adhesiveness of the enzyme, it is preferable to use the plastic tube).

The activity is calculated using the following formulae:

Volume activity U/ml={ΔOD/min(ΔOD test−ΔOD blank)×$Vt×df$}/(1.04×1.0×$Vs$)

Weight activity U/mg=(U/ml)×1/$C$

Vt: total volume (3.1 mL)
Vs: sample volume (1.0 mL)
1.04: mM molecular absorbance coefficient of potassium ferricyanide
1.0: light path length (cm)
df: dilution coefficient
C: enzyme concentration in solution (c mg/mL)

Measurement of Specific Activity

The amount of the protein contained in unit liquid amount was measured by protein assay whose principle was Bradford method. Actually, Protein Assay kit supplied from Bio-Rad was used in accordance with its protocol. The enzyme solution (0.1 mL) was added to the commercially available staining solution (5 mL) diluted 5 times, mixed, left stand at room temperature for 30 minutes, and then the absorbance at a wavelength of 595 nm was measured. At that time, the working curve was made by measuring bovine serum albumin at known concentrations by the same method, and using that, the amount of the protein contained in the enzyme solution was calculated per unit liquid amount.

Meanwhile, the activity value per unit liquid amount was measured by the above method of measuring the activity, and the specific activity of pyrroloquinoline quinone dependent glucose dehydrogenase was calculated by dividing the activity value per unit liquid amount by the protein amount per unit liquid amount.

The results are shown in Table 202.

TABLE 202

| Mutation | specific activity |
|---|---|
| wild type | 1.0 |
| Q168A | 8.6 |
| Q168A + L169G | 2.5 |
| Q168A + L169C | 1.9 |
| Q168A + L169P | 20.1 |
| Q168S + L169E | 1.1 |
| Q168S + L169P | 13.1 |

As a result of measuring the specific activity, when the enzyme activity was measured using the ferricyanide ion as the mediator, all modified types of pyrroloquinoline quinone dependent glucose dehydrogenase exhibited the increased specific activity compared with the wild type enzyme.

The following speculative theories are possible for the reason why the specific activity is increased by deleting, substituting or adding one or more amino acids in the amino acid sequence of the wild type pyrroloquinoline quinone dependent glucose dehydrogenase.

In the detail reaction mechanism of pyrroloquinoline quinone dependent glucose dehydrogenase, D-glucose as the substrate is oxidized, the electron is transferred to pyrroloquinoline quinone coordinated to oxygen, and further transferred to the ferricyanide ion as the mediator. It is thought that a rate controlling point of the enzyme reaction is the process in which the electron is transferred to the ferricyanide ion as the mediator because the reactivity from pyrroloquinoline quinone to the ferricyanide ion is low.

For example, supposing the case in which the amino acid in the vicinity of the active center has been mutated, then, the three dimensional structure of the enzyme in the vicinity of the active center including the active center is changed and the ferricyanide ion easily enters. Thus the electron transfer to the ferricyanide ion which is the rate controlling stage of the enzyme reaction becomes smooth, and consequently the specific activity appears to be enhanced.

That is, it is speculated that the enhancement of the specific activity can be expected in the enzyme activity measurement using the ferricyanide ion as the mediator by substituting/mutating one or more amino acid in the vicinity of the active center. Alternatively, in another viewpoint, in the present invention, it is desirable to mutate the amino acid present within a radius of 10 angstroms from the active center.

The amino acids in the vicinity of the active center specifically include the amino acids located at positions 76, 143, 144, 163, 168, 169, 228, 229, 247, 248, 343, 346, 348, 377, 406, 408 and 424 (e.g., see Non-patent document 5)

Non-patent document 5: Protein Science (2000), 9:1265-1273

Example 202

It is specifically described using the modified pyrroloquinoline quinone dependent glucose dehydrogenase of (Q168A+L169G+E245D) and (Q168A+L169P+E245D) that the enhancement effect of the specific activity confirmed in Example 201 is kept even when the substitution of the amino acid in the non-vicinity of the active center is added. Needless to say, the present invention is not limited to the following Example.

The purified enzyme preparations of modified pyrroloquinoline quinone dependent glucose dehydrogenase of (Q168A+L169G+E245D) and (Q168A+L169P+E245D) were obtained and their performances were evaluated by the same ways as in Example 201. A recombinant plasmid (pNPG5M168A+169G+E245D) encoding the mutant PQQ dependent glucose dehydrogenase in which glutamine at position 168 had been substituted with alanine, leucine at position 169 had been substituted with glycine and glutamic acid at 245 had been substituted with aspartic acid in the amino acid sequence described in SEQ ID NO:1 was made based on pNPG5M168A+169G, a synthetic oligonucleotide described in SEQ ID NO:94 and a synthetic oligonucleotide complementary thereto. Likewise, a recombinant plasmid (pNPG5M168A+169P+E245D) encoding the mutant PQQ dependent glucose dehydrogenase in which glutamine at position 168 had been substituted with alanine, leucine at position 169 had been substituted with proline and glutamic acid at 245 had been substituted with aspartic acid in the amino acid sequence described in SEQ ID NO:1 was made based on pNPG5M168A+169P. The expression vectors were constructed, the transformants of bacteria belonging to the genus Pseudomonas were made, the holo type expression purified enzymes were prepared, and their performances were evaluated by treating these recombinant plasmids by the same ways as in Example 201. The results are shown in Table 203

TABLE 203

| Mutation | specific activity (U/mL) |
| --- | --- |
| Wild type | 0.9 |
| Q168A + L169G + E245D | 7.8 |
| Q168A + L169P + E245D | 22.8 |

From the results in Example 202, it has been confirmed that the amino acid substitution introduced into the site which is not in the vicinity of the active center does not prevent the enhancement effect of the specific activity due to the amino acid substitution introduced in the vicinity of the active center.

INDUSTRIAL APPLICABILITY

According to the present invention, it is possible to obtain PQQGDH having the improved substrate specificity, and preferably PQQGDH also having the improved thermal stability. This modified PQQGDH can be utilized for the glucose assay kit and the glucose sensor.

The modified pyrroloquinoline quinone dependent glucose dehydrogenase enables to decrease the amount of the enzyme to be added to the assay system by enhancing the specific activity, and therefore it is possible to inexpensively produce the glucose assay kit and the glucose sensor using the ferricyanide ion as the mediator. The present invention can be utilized for broad fields for intended use such as clinical laboratory tests and food analyses, and largely contributes to the industry.

The invention claimed is:

1. An isolated modified pyrroloquinoline quinone dependent glucose dehydrogenase (PQQGDH) consisting of SEQ ID NO: 1 except that
   (a) the glutamine at position 168 is substituted with an amino acid other than glutamine, and
   (b) the leucine at position 169 is substituted with an amino acid other than leucine
   wherein the modified PQQGDH has less dehydrogenase activity on a disaccharide than wild type PQQGDH consisting of SEQ ID NO: 1 without any modifications.

2. The modified pyrroloquinoline quinone dependent glucose dehydrogenase (PQQGDH) according to claim 1, which has more thermal stability than the wild type PQQGDH.

3. A gene encoding the modified PQQGDH according to claim 1.

4. A vector comprising the gene according to claim 3.

5. A transformant transformed with the vector according to claim 4.

6. A method of producing modified PQQGDH characterized by culturing the transformant according to claim 5.

7. A glucose assay kit comprising the modified PQQGDH according to claim 1.

8. A glucose sensor comprising the modified PQQGDH according to claim 1.

9. A method of measuring glucose comprising the modified PQQGDH according to claim 1.

* * * * *